(12) United States Patent
Quiros et al.

(10) Patent No.: US 7,250,559 B2
(45) Date of Patent: Jul. 31, 2007

(54) NUCLEIC ACIDS ENCODING GLUCOSINOLATE BIOSYNTHESIS ENZYMES AND METHODS OF THEIR USE

(75) Inventors: Carlos Quiros, Davis, CA (US); Genyi Li, Winnipeg (CA)

(73) Assignee: Regents of the University of California, Oakland, CA (US)

( * ) Notice: Subject to any disclaimer, the term of this patent is extended or adjusted under 35 U.S.C. 154(b) by 211 days.

(21) Appl. No.: 10/482,951

(22) PCT Filed: Jul. 5, 2002

(86) PCT No.: PCT/US02/21408

§ 371 (c)(1),
(2), (4) Date: Oct. 1, 2004

(87) PCT Pub. No.: WO03/004619

PCT Pub. Date: Jan. 16, 2003

(65) Prior Publication Data

US 2005/0055744 A1    Mar. 10, 2005

Related U.S. Application Data

(60) Provisional application No. 60/303,310, filed on Jul. 5, 2001.

(51) Int. Cl.
*A01H 5/00* (2006.01)
*C12N 15/82* (2006.01)
*C12N 15/29* (2006.01)

(52) U.S. Cl. .................. 800/298; 435/320.1; 435/419; 536/23.6; 800/278

(58) Field of Classification Search .................... None
See application file for complete search history.

(56) References Cited

OTHER PUBLICATIONS

Mikkelsen et al. Cytochrome P450 CYP79B2 from Arabidopsis catalyzes the conversion of tryptophan to indole-3-acetaldoxime, a precursor of indole glucosinolates and indole-3-acetic acid. (2000) JBC, vol. 275, pp. 33712-33717.*
Keskin et al. (Protein Science, 13:1043-1055, 2004).*
Guo et al. (PNAS, 101: 9205-9210, 2004).*
Thornton et al. (Nature structural Biology, structural genomics supplement, Nov. 2000).*
Database GenCore on EST, Kaneko, et al.; "Structural analysis of Aribidopsis thaliana chromosome"; direct submission to EMBL/GenBank/DDBJ databases: ID No. Q9FG67, Gene Sequence; Apr. 1999.
Database GenCore on EST, Kroymann, et al.; "A MYB transciption factor and a gene similar to MYJ24.1 are encoded in the regions between MRN17 and MY2"; direct submission to EMBL/GenBank/DDBJ databases; ID No. Q8VX04, Gene Sequence; Mar. 1999.
Li, G., et al.; "Inheritance of three major genes involved in the synthesis of aliphatic glucosinolates in *Brassica oleracea*"; *J. Amer. Soc. Hort. Sci.*; 2001; pp. 427-431; vol. 126, No. 4.
Heneen, W.K., et al.; "Characterization of the A and C genomes of *Brassica campestris* and *B. alboglabra*"; *Hereditas*; 1995; pp. 251-267; vol. 123.
Fahey, Jed W., et al.; "Broccoli sprouts; an exceptionally rich source of enzymes that protect against chemical carcinogens"; *Proc. Natl. Acad. Sci. USA*; Sep. 1997; pp, 10367-10372; vol. 94, No. 19; The National Academy of Sciences.

* cited by examiner

Primary Examiner—David H. Kruse
Assistant Examiner—Vinod Kumar
(74) Attorney, Agent, or Firm—Townsend and Townsend and Crew LLP

(57) ABSTRACT

Provided are nucleic acid sequences from *Brassica oleracea* plants that encode enzymes involved in the synthesis of a glucosinolate molecule, including BoGSL-ALK, and BoGSL-ELONG, and methods of their use. The sequences find particular use in modifying the glucosinolate content of a plant. Also provided are primers for these two genes and a third key gene in the glucosinolate pathway, BoGSL-PRO, that can be used for developing molecular markers for assisted selection of plants with specific glucosinolate compositions. Additionally, compositions and methods for a simple, reliable and efficient PCR-based marker system, named sequence-related amplification polymorphism (SRAP), that finds use in the identification of coding sequences in the genome of a plant are provided.

17 Claims, 6 Drawing Sheets

Figure 3

NUCLEIC ACIDS ENCODING GLUCOSINOLATE BIOSYNTHESIS ENZYMES AND METHODS OF THEIR USE

STATEMENT AS TO RIGHTS TO INVENTIONS MADE UNDER FEDERALLY SPONSORED RESEARCH AND DEVELOPMENT

This invention was made with Government support under Grant No. 9736215-5254, awarded by the United States Department of Agriculture. The Government has certain rights in this invention.

CROSS-REFERENCES TO RELATED APPLICATIONS

The present is a non-provisional filing of U.S. Provisional Patent Application No. 60/303,310, which was filed on Jul. 5, 2001. Priority is claimed to the provisional application, which is incorporated herein by reference in its entirety for all purposes.

BACKGROUND OF THE INVENTION

1. Field of the Invention

The invention relates to compositions and methods of using nucleic acids and amino acids that encode enzymes involved in the synthesis of glucosinolates (GSL). The invention is exemplified by nucleic acids and amino acids encoding a BoGSL-ALK, an enzyme involved in glucosinolate side-chain desaturation, isolated from *Brassica oleracea* (Groups *Botrytis* (Cauliflower and Broccoli), *Italica* (Broccoli) and *Viridis* (Collard)), and methods of using these sequences to increase or decrease the levels of alkenyl glucosinolates in *Brassica oleracea* plant varieties. The invention also relates to methods and compositions for marker assisted gene selection, exemplified by primers and methods of using them for selecting BoGSL-ALK and two other key genes in GSL synthesis, BoGSL-PRO and BoGSL-ELONG.

2. Introduction

GSL are a diverse class of thioglucosides that are synthesized by many species of the order Capparales, including *Brassica* and *Arabidopsis* Heynh. The GSL molecule consists of two parts; a common glycone moiety and a variable aglycone side chain (Fenwick et al., *Crit. Rev. Food Sci. Nutr.*, 18:123-301 (1983); Rosa et al., *Hort Rev,* 19:99-215 (1997)). The aglycone part may contain aliphatic, indolyl, or aromatic side chains and is derived from a corresponding α-amino acid. In the general GSL biosynthetic pathway proposed by Underhill, Glucosinolates. *Encyclopedia of Plant Physiology* (New Series), Vol. 8, Springer Verlag, Berlin, pp. 493-511 (1980); Larsen, Glucosinolates. In: *The Biochemistry of Plants* (EE Conn, ed.), Vol. 7, Academic Press, New York, pp. 501-525 (1981); and Haughn et al., *Plant Physiol,* 97:217-226 (1991), aliphatic GSL are derived from methionine. Genetic studies in *Arabidopsis thaliana* (Mithen et al., *Heredity,* 74:210-215 (1995); Mithen and Campos, *Entomol. Exp. Appl.,* 80:202-205 (1996)) and *Brassica* sp. (Magrath et al., *Plant Breeding,* 111:55-72 (1993); Magrath et al., *Heredity,* 72:290-299 (1994)) support the biochemical pathway proposed for biosynthesis of aliphatic GSL. The synthesis of these compounds is determined by a simple genetic system containing two distinct sets of genes, one determining side-chain elongation and the second one for chemical modification of the side-chains. Aliphatic GSL profiles vary considerably in *A. thaliana* ecotypes and in *Brassica* crops and species. These GSL are synthesized in the following sequence: methylsulfinylalkyl, alkenyl and hydroxy-types, which can be divided into three-carbon (3C) four-carbon (4C) and five-carbon (5C) groups based on their side-chain length.

A number of studies suggest that consumption of vegetables, in particular, crops such as broccoli [*Brassica oleraca (Italica* Group)] and other crucifers, reduces the incidence of cancer in humans and other mammals (Block et al., *Nutr. Cancer,* 18:1-29 (1992); Fahey and Talalay (1998) pp. 16-22. In: T. Shibamoto, J. Terao and T. Osawa (eds.). *Functional foods for disease prevention I. Fruits, vegetables and teas.*, Amer. Chem. Soc. Symp. Ser., 701. Amer. Chem. Soc., Washington, D.C.; Prochaska et al., *Proc. Natl. Acad. Sci. USA,* 89:2394-2398 (1992)). This seems to be due to the presence of inducers of phase II enzymes, that detoxify carcinogens and mutagens in various mammalian organs (Prestera et al., *Adv. Enzyme Regulat.,* 33:28 1-296 (1996); Prochaska et al., (1992) supra; Talalay et al., pp. 469-478 (1992). In: L. W. Wattenberg, M. Lipkin, C. W. Boone, and G. J. Kelloff, (eds.). Cancer chemoprevention, CRC Press, Boca Raton, Fla.). In broccoli, the isothiocyanate sulfurophane, derived from the GSL glucoraphanin by the action of the enzyme myrosinase, was identified as a potent inducer of these enzymes, conferring protection against mammary tumor growth in rats after treatment with dimethyl benzanthracene, a carcinogenic agent (Zhang et al., *Proc. Natl. Acad. Sci. USA,* 91:3147-3150 (1994)). Glucoraphanin is one of the major GSL present in some crops of *B. oleracea* such as broccoli (Farnham et al., *J. Amer. Soc. Hort. Sci.,* 125:482-488 (2000)) cauliflower, [*B. oleraca (Botrytis* Group)], cabbage [*B. oleraca (Capitata* Group)] and brussels sprouts [*B. oleraca (Gemmifera* Group)] (Rosa et al., *Hort Rev,* 19:99-215 (1997)). Unfortunately, the wide range of glucoraphanin in broccoli can lead to consumer confusion. At the present time the consumer that eats broccoli might assume that it has high sulfurophane content and that therefore this produce is conferring health benefits by carcinogen detoxification. However, this is not always true. For example, the heads of broccoli inbred plants have been found to contain from 0.28 to 4.0 mol/gram of fresh weight glucoraphanin content (Farnham, et al. (2000) *J. Amer. Soc. Hort. Sci.* 125(4):482-488). Because most of the existing broccoli varieties in the supermarket have not been selected for glucoraphanin content, the precursor of sulfurophane, certain produce could actually possess only small concentrations of this compound and in reality be ineffective for its assumed anticarcinogenic properties.

Although certain GSL derivatives have a protective effect against cancer (Rosa et al., (1997) supra), there are some that may have detrimental effects such those derived from alkenyl GSL in rapeseed seed meal (*Brassica napus L.*). Such GSLs act as anti-nutrients affecting not only animal growth and development, but also lowering food intake. Additionally, modified isothiocyanates from the aliphatic GSL progoitrin may have goitrogenic effects in animals (Rosa et al., (1997) supra). There is therefore an interest in methods and compositions for lowering the amount of these antinutritional GSL and for providing crucifer varieties with consistently increased amounts of protective GSL in plants intended for human and animal consumption.

The polymerase chain reaction (PCR) is widely used in genomic DNA analysis. One of its main applications has been on the development of DNA markers for map construction, which are useful in breeding, taxonomy, evolution and gene cloning. Several PCR marker systems are available varying in complexity, reliability and information generating capacity. These include random amplified polymorphic DNA (RAPD), simple sequence repeat polymorphism (SSR), amplified fragment length polymorphism (AFLP) and a few others (Lee, *Adv. Agronomy*, 55:265-344 (1995); Rafalski et al., in Non Mammalian genome analysis: A practical guide, Acad. Press, pp. 75-134 (1996)). Each system has its own advantages and disadvantages. For example, RAPD is a simple method to fingerprint genomic DNA, but poor consistency and low multiplexing output limit its use. SSR has the advantage that it produces mostly co-dominant markers, however the development of these is expensive and time-consuming. AFLPs are now widely used for a variety of applications due to their high multiplexing ratio (Vos et al., *Nucleic Acids Res*, 23:4407-4414 (1995)). The main disadvantage of this method is its complexity, it being necessary to perform multiple steps including DNA digestion, ligation and amplification, which makes it difficult to optimize the conditions for each step. Furthermore, methylation of genomic DNA can result in pseudo polymorphism when the restriction enzyme used is methylation-sensitive. Also the use of the MseI restriction enzyme, which recognizes AATT restriction sites, often results in uneven marker distribution in the genome of some species (Haanstra et al., *Theor Appl Genet*, 99:254-271 (1999)). Ability to isolate specific bands for sequencing is another concern when selecting a marker system, especially for the development of new markers for gene tagging. In most cases, both RAPD and AFLP markers need to be cloned into vectors, which adds to the labor. In addition, for AFLP bands it is notoriously difficult to isolate the correct fragment due to band overlapping. Therefore, there is a need for a PCR marker system that combines the desired attributes of simplicity, reliability, moderate throughput ratio, facile sequencing of selected band, with targeting of coding sequences in the genome and efficient identification of a moderate number of co-dominant markers.

3. Relevant Literature

*Brassica napus* seeds, and plants producing them, obtained by genetic mutation and having a maximum total glucosinolate content of about 3.4 micromoles per gram of seed and a maximum 4-hydroxy-3-indolylmethyl glucosinolate content of 1.9 micromoles per gram of seed are disclosed in U.S. Pat. No. 6,225,533.

In *Arabidopsis thaliana*, several genes involved in the glucosinolate pathway have been identified by genetic analysis (Mithen et al., *Heredity*, 74:210-215 (1995); Mithen and Campos, *Entomol. Exp Appl.*, 80:202-205 (1996)). In rapeseed, genes regulating aglycon side-chain elongation and modification have been reported (Magrath et al., *Plant Breeding*, 111:55-72 (1993); Parkin, et al. (1994) *Heredity* 72:594-598 (1994)). Campos de Quiros et al., *Theoretical and Applied Genetics*, 101:429-437 (2000)) disclose the mapping and sequencing of a GSL-ELONG gene from *A. thaliana*. However, many steps in side-chain elongation, glycone formation, and aglycone modification remain to be characterized biochemically and genetically.

Hall et al., *Theoretical and Applied Genetics*, 102:369-374 (2001)) disclose the fine mapping of the OHP locus in *A. thaliana*, which contains a gene cluster of three open reading frames with high homology to sequences encoding 2-oxoglutarate-dependent dioxygenases (2-ODDs). The 2-ODD translation products associate with glucosinolate hydroxylation activity, and Hall speculates that the ALK and OHP loci in *A. thaliana* may either represent two closely linked genes or different alleles of the same gene. Hall et al. do not provide either a nucleic acid or an amino acid sequence. Kliebenstein et al., *Plant Cell*, 13:681-693 (2001)) disclose the identification of genes encoding two 2-oxoglutarate-dependent dioxygenases from *Arabidopsis* that control the conversion of methylsulfinylalkyl glucosinolate to either the alkenyl or the hydroxyalkyl form. Kliebenstein et al. expressed these genes in *E. coli* to determine their catalytic activity. WO 99/27120 discloses cloning of GSL-ELONGASE gene alleles from *Arabidopsis*.

SUMMARY OF THE INVENTION

Compositions and methods are provided for modifying the glucosinolate content of a plant or plant cell using one or more enzyme involved in the modification or biosynthesis of a glucosinolate compound. The methods include the steps of transforming a plant or plant cell with a construct that comprises a nucleic acid encoding an enzyme required for the modification of a glucosinolate, and growing the plant or plant cell, whereby the nucleic acid sequence is transcribed in either the sense or antisense orientation to increase or decrease the activity of glucosinolate side-chain elongation, desaturation/alkenylation and/or hydroxylation as desired. The compositions include constructs and vectors that contain the nucleic acid, and cells, particularly plant cells, that contain such constructs or vectors. Particular nucleic acids provided include the DNA sequences for BoGSL-ALK from *Brassica oleracea* and the *Brassica oleracea* homologue BoGLS-ELONG from broccoli. The invention finds use in improving the nutritional value of a plant that produces glucosinolate compounds, such as those of the order Capparales, including *Brassica* and *Arabidopsis*, and for rationally controlling the glucosinolate content of a plant.

Also provided is a simplified high throughput marker system, called Sequence-Related Amplified Polymorphism (SRAP), that can be used for map construction, gene tagging, genomic and cDNA fingerprinting and map based cloning and primer pairs designed to carry out this marker system. In using the SRAP marker system, a primer pair is used to preferentially amplify a coding sequence from the genomic DNA of a plant. The "amplicons" or sequences amplified by a particular primer pair are amplified in a polymerase reaction, separated, and sequenced. The SRAP marker identification system is applicable to any monocotyledonous or dicotyledonous plant, particularly vegetable, fruit, and grain plants such as wheat and corn. The molecular markers can be used for visual selection of plants with a specific genetic profile, such as a glucosinolate profile.

DESCRIPTION OF THE DRAWINGS

FIG. 3 shows a ClustalW alignment of BoGSL-ALK (BOALK) amino acid sequences from collard (SEQ ID NO:40) with corresponding functional *A. thaliana* homolog from ecotype Cape Verde Islands (Atcvi2) (SEQ ID NO:39), and to predicted products of duplicate *Arabidopsis* ODD genes ODD1 from ecotype Columbia (Atcol1) (SEQ ID NO:41) and ODD3 from ecotypes Landsberg (Atler3) (SEQ ID NO:38) and Cape Verde Islands (Atcvi3) (SEQ ID NO:37). Shading designates conserved amino acids.

DESCRIPTION OF THE SPECIFIC EMBODIMENTS

Figure 1:
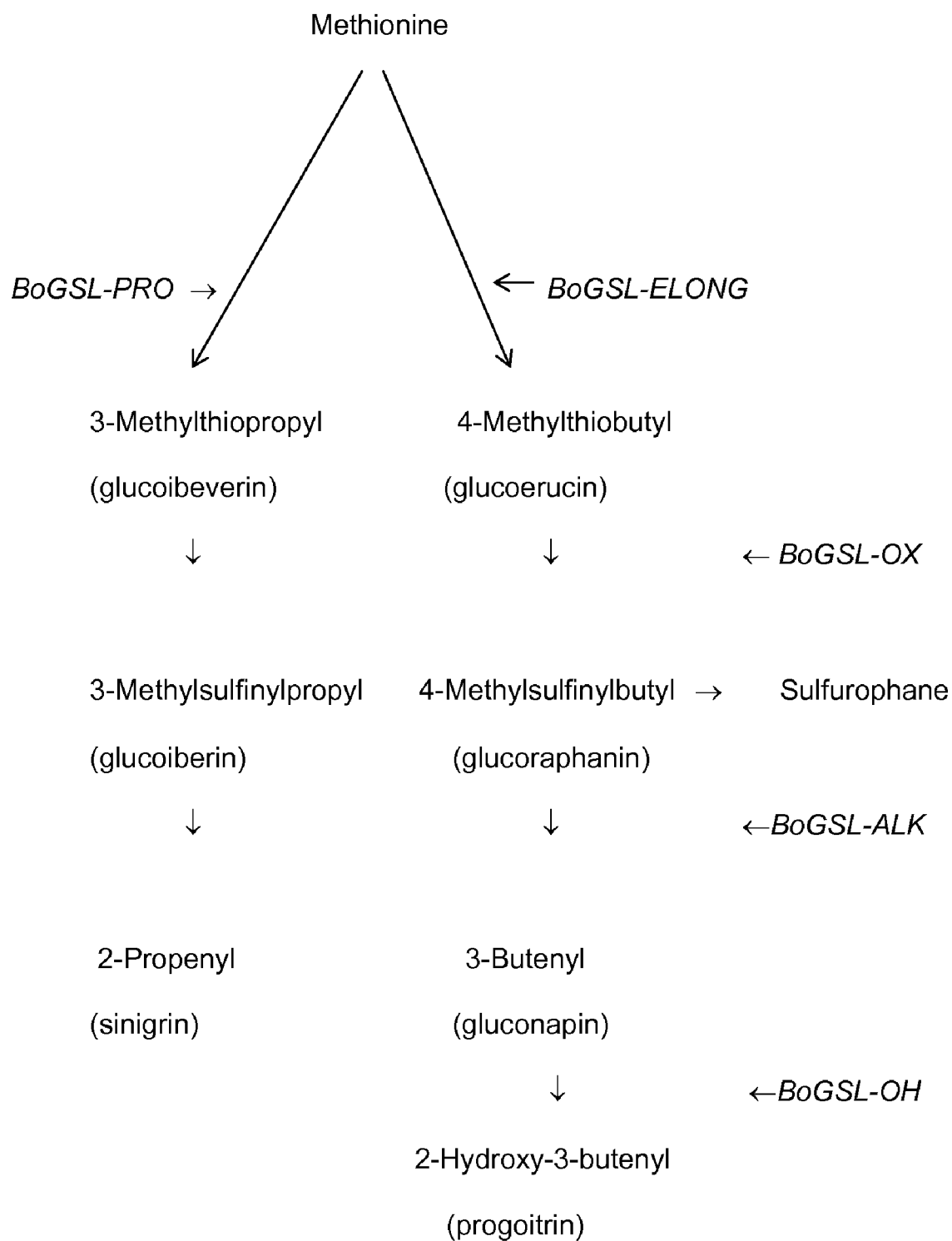
FIG. 1 shows the aliphatic glucosinolate pathway.
Figure 2:
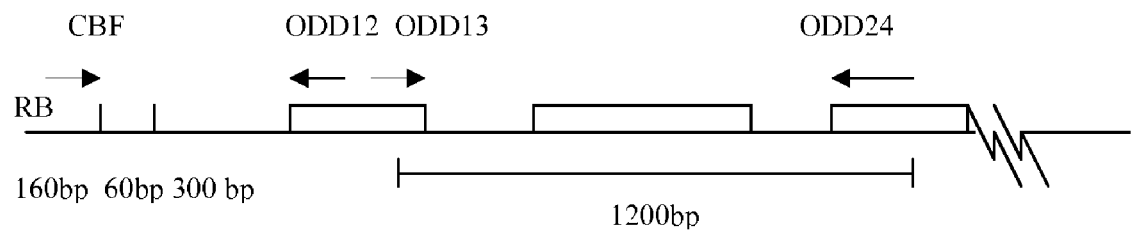
FIG. 2 shows a schematic representation of primer locations (arrows) of CBF, ODD12, ODD13 and ODD24 in vector and BoGSL-ALK+ allele. RB, right border in T-DNA from vector, boxes indicate the first three exons of BoGSL-ALK+.
Figure 4:
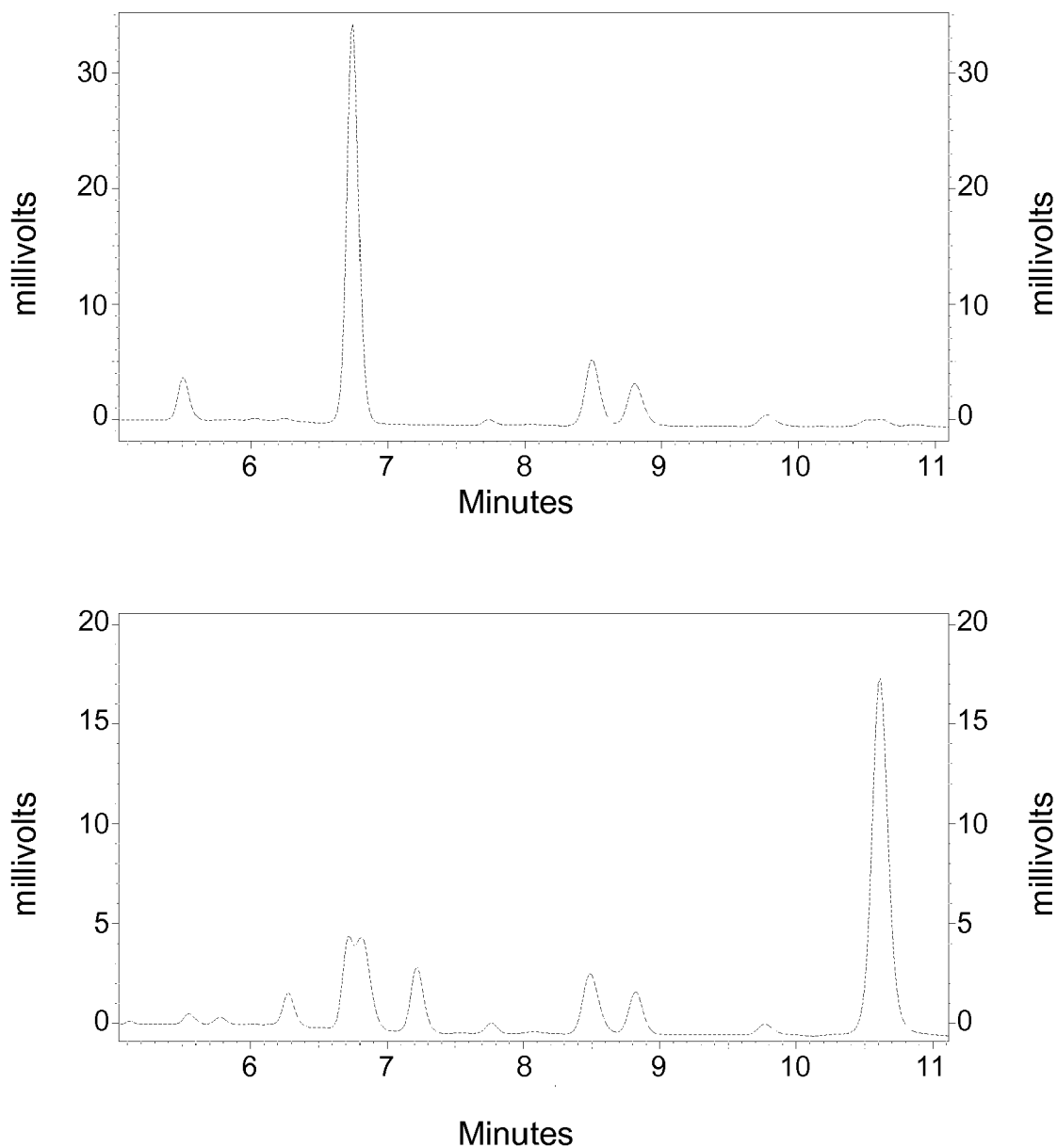
FIG. 4 shows GSL profiles for transformed and wild type *A. thaliana* ecotype Columbia. A. GSL profile wild type ecotype lacking a functional GSL-ALK allele displays two main aliphatic GSL, 3-carbon 3-Methylsulfinylpropyl (glucoiberin, peak 1) and 4-carbon 4-Methylsulfinylbutyl (glucoraphanin, peak 3). B. Transformed Columbia plants with functional BoGSL-ALK allele display reduced concentration of precursor 3-Methylsulfinylpropyl (peak 1), which is converted to 2-Propenyl (sinigrin, peak 4), and reduced concentration of precursor 4-Methylsulfinylbutyl (peak 3), which is converted into 3-Butenyl (gluconapin, peak 5). Presence of 2-hydroxy-3-butenyl (progoitrin, peak 2), indicates activity of the allele at the GSL-OH locus (see FIG. 1). Peak 3, which shows a double peak includes 4-Methylsulfinylbutyl and 2 (S)-hydroxy-3-butenyl, a derivative from 3-Butenyl (peak 5).(see, Mithen et al. (1995) *Heredity* 74:210).
Figure 5:
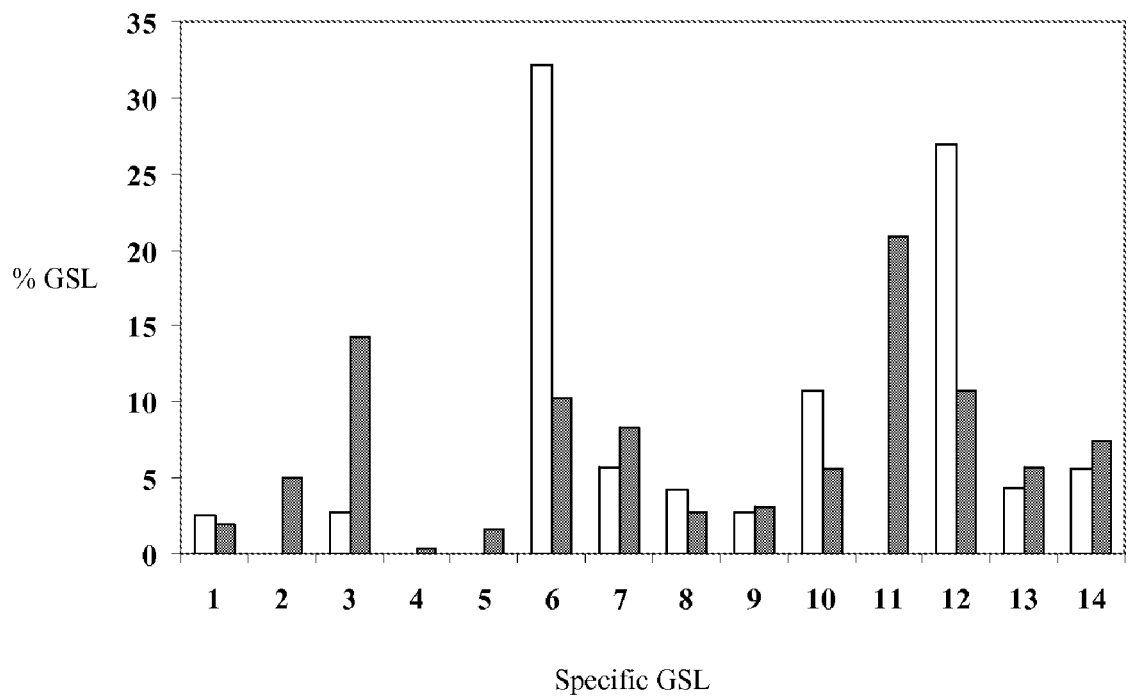
FIG. 5 shows relative amounts (expressed in percentage) of main glucosinolate (GSL) for seeds of transformed (shaded bars) and wild type *A. thaliana* ecotype Columbia (clear bars). Bar 1: 3-methylsulfinylpropyl, 2: 2-hydroxy-3-butenyl, 3: 4-methylsulfinylbutyl, 4: 2-Propenyl, 5: 3-butenyl, 6: 4-methylthiobutyl, 7: 8-methylsulfinyloctyl, 8: indolyl-3-methyl, 9: 5-methylthiopentyl; 10: 3-benzoyloxypropyl; 11: 2-benzoyloxy-3-butenyl; 12: 4-benzoyloxybutyl; 13: 7-methylthioheptyl; 14: 8-methylthioctyl.
Figure 6:
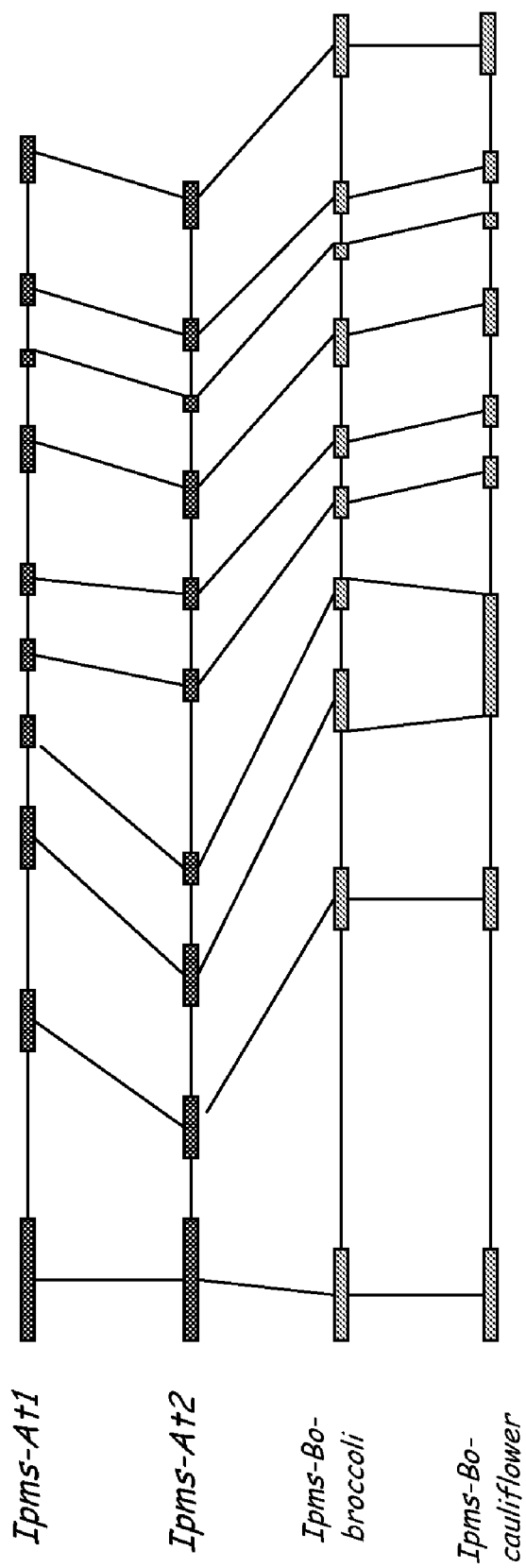
FIG. 6 shows a diagrammatic representation at approximate scale of IPMS genes in *Arabidopsis* and the two *Brassica* alleles homologous to these genes. Boxes represent exons. In the cauliflower allele exons 3 and 4 are fused due to a splicing mutation (diagram based on Kroymann et al. (2001) *Plant Phys.* 127:1077.

Compositions and methods are provided for the modification of the total glucosinolate content of a plant or plant cell of interest, particularly a crucifer such as broccoli, cauliflower, cabbage or brussel sprouts, in edible plant tissues such as flowers, leaves and seed, as well as the content of particular glucosinolates. By "glucosinolate molecule", "glucosinolate compound", "glucosinolate" or "thioglucoside" is intended the commonly understood definition by those in the art of the secondary metabolites by structure and function, wherein a glucosinolate structure is comprised of a common glycone moiety and a variable aglycone side chain. By "modification of total glucosinolate content" is intended both qualitative and quantitative modification of a plant glucosinolate profile, where quantitative modification refers to the amount of total or particular glucosinolates and qualitative modification refers to the presence or absence of particular glucosinolate molecules. Qualitative modification of glucosinolate side chains relates to increasing or decreasing side chain length, saturation, alkenylation, hydroxylation, oxidation, sulfinylation and the like. The amount of particular glucosinolates can be modified by expressing the relevant genes in either the sense or antisense orientation depending on the intended modification. As an example, glucoraphanin and sinigrin can be increased to 2- to 5-fold in plants that already contain these compounds, such as cabbage. In plants that lack glucoraphanin, such as cauliflower, the concentration can be increased to about 2-3 mol/gram of tissue (fresh weight) or more. The modification can also includes decreasing total glucosinolates and/or eliminating particular glucosinolates such as those derived from alkenyl glucosinolates. As an example, progoitrin can be decreased to less than about 1.0 mol/gram fresh weight of rapeseed seeds.

In the method used, one or more genes encoding enzymes involved in the biosynthesis or modification of a glucosinolate side chain by catalyzing reactions that alter the extent of glucosinolate side-chain elongation, and/or desaturation and/or hydroxylation is introduced into a plant or plant cell of interest. The plant or plant cell of interest can be chosen using the marker system described herein. Primers for three major genes in glucosinolate biosynthesis in *Brassica* crops, BoGSL-ALK, BoGSL-PRO and BoGSL-ELONG have been developed using this method and can be used to visually select plants with specific glucosinolate profiles, i.e., containing or lacking certain glucosinolates. The constructs used for plant transformation are designed to include single or multiple expression cassettes, each comprised of a promoter, generally a tissue specific promoter for preferential expression for example in seed, leaves or fruit although constitutive promoters such as the 35S or double 35S can be used, operably linked to a nucleic acid coding for a glucosinolate-modifying enzyme.

Aliphatic GSL are classified by side-chain size as 3-carbon (3C), 4-carbon (4C) and 5-carbon (5C) GSL. They also can be classified by side-chain structure into methylthioalkyl, methylsulfinylalkyl, alkenyl and hydroxyalkenyl glucosinolates. Examples of enzymes that can be used to manipulate the glucosinolate biosynthesis pathway in plants include BoGSL-ELONG, BoGSL-ALK, BoGSL-PRO, BoGSL-OXID and BoGSL-OH genes from broccoli and collard and other *Brassica oleracea* plant varieties, as well as related enzymes from ecotypes such as *Arabidopsis thaliana*. GSL-ELONG and GSL-PRO determine length of the side-chains, where a dominant GSL-ELONG allele favors 4C side-chains and a dominant GSL-PRO favors 3C side chains. BoGSL-OXID, BoGSL-ALK, and BoGSL-OH are side-chain modification enzymes. For example, GSL-OXID catalyzes the conversion of methylthioalkyl into methylsulfinylalkyl; GSL-ALK induces alkenyl GSL through desaturation and loss of the methylsulfenyl moiety. Alkenylated GSL species can be transformed by GSL-OH into hydroxyalkenyl GSL. Combinations of functional or null alleles at each locus, or the transcription of antisense sequence segments of functional alleles, can be used to rationally create a preferred GSL composition of in a *Brassica* species.

The subject invention offers several advantages in the engineering of crops to alter the content of specific glucosinolates (GSL). Although it was possible to alter glucosinolate content to a certain extent by conventional breeding, it is now possible to do this type of manipulation in any *Brassica* crop or species, and it also can be extended to species of other genera. Previously, the breeder was limited to reducing total glucosinolates, such has been done in the case of Canola, an oilseed crop, or to increasing by selection glucoraphanin content in broccoli or sinigrin levels in cauliflower. In the subject invention, downregulation or inactivation of the BoGSL-ALK gene leads to accumulation of glucoraphanin, a source of anticarcinogenic isothyocianates, and reduction or elimination of progoitrin, an antinutrient with goitrogenic ability. In other embodiments, upregulation or activation of this gene leads to the production of sinigrin, a compound possessing antifungal properties and possible action as a nematocide. The antifungal and nematocidal properties of plants possessing high levels of sinigrin are useful not only in protecting the plants themselves but also in protecting companion plants, for instance, when used as a ground cover crop or incorporated into the soil as green manure. Genetic manipulation using the BoGSL-ALK gene allows virtual elimination of glucosinolates with antinutrient properties, such as progoitrin, which can not be achieved by conventional breeding. The use of the BoGSL-ALK, together with the genes encoding enzymes involved in 3C and 4C side chain elongation allows construction of plants from any *Brassica* crop containing or lacking specific glucosinolates. A myriad of different glucosinolate compositions can be engineered in a particular host plant by transforming the plant with one or more genes encoding enzymes that catalyze distinct reactions in the glucosinolate biosynthesis pathways, each in either the sense or antisense orientation. Recombinant expression of glucosinolate modifying enzymes presents conveniences and efficiencies that are not realized when using traditional breeding methods. Producing transgenic plants allows identifying a host plant with the desired glucosinolate composition within a shorter period of time, with greater flexibility and control in the introduction and selective expression of multiple genes to achieve a particular desired glucosinolate composition. The SRAP PCR marker system is advantageous in the application of identifying open reading frames, mapping and tagging genes, and in cDNA fingerprinting because it is simple to carry out, reliable, and allows a moderate throughput ratio and facile sequencing of selected bands.

Other advantages include the application of the SRAP method of the invention to cDNA fingerprinting from specific tissues as a simpler alternative to differential display. The SRAP PCR marker method is used not only for genomic DNA but also for cDNA genetic mapping. This is different from EST mapping (based on DNA hybridization) because the method is based on polymorphisms detected by fingerprinting cDNAs directly by amplification using SRAP primers. The SRAP marker method is useful for finding the position of a gene of interest in relation to the locations of gene homologues in other genomes, such as an *Arabidopsis* genome. Phenotypes for specific traits are associated directly with their corresponding cDNA marker, allowing identification of a candidate gene in a simpler manner. Using these tools along with a BAC library allows isolation and cloning of any desired gene. Based on the application of this system, two other key genes in the aliphatic glucosinolate pathway in addition to BoGSL-ALK were tagged, BoGSL-PRO and BoGSL-ELONG, by construction of specific markers.

An advantage of the primers developed is that they can be used to amplify plant DNA for any of the genes BoGSL-ALK, BoGSL-PRO and BoGSL-ELONG in *B. oleracea* populations segregating for the broccoli alleles of these genes. The use of these markers will allow visual selection of specific genotypes for each of the three genes. The primers disclosed, or similar primers developed from the original sequences of BoGSL-ALK and BoGSL-ELONG can be used to construct primers for selection of *Brassica oleracea* plants with a high content of glucoraphanin, a precursor for an anticarcinogenic agent, by selecting for plants carrying a BoGSL-ALK antisense segment or null allele. Identification of BoGSL-ALK null alleles also can be used for selection of plants lacking progoitrin in vegetable *Brassicas* and rapeseed (Canola), which is considered an antinutrient causing goitrogenic disorders. Selection can also be made for plants that synthesize high levels of sinigrin, a precursor for a natural fungicide, nematocide and weed suppressor, by selecting for plants that have a BoGSL-ELONG antisense segment or null allele, such as is found in cauliflower.

The primers offer the advantage that plants with specific glucosinolate compositions can be selected visually, which will allow the development of new varieties of crucifers with specific nutraceutical content and other useful secondary metabolites. Development of plant varieties with a specific content of nutraceuticals is now an important objective of seed and biotechnology companies. Current techniques for the selection of specific glucosinolate profiles is complex and unpredictable, since extensive chemical analysis of progeny plants must be done. The visual selection of specific alleles for each gene offers the advantage that it is more precise, efficient and less costly than current techniques. For use in marker assisted breeding, ODD14 5'-TCG-GTCTTTGTCGTTTTCTA-3' (SEQ ID NO:29) and ODD15 5'-GCGAGGATGCTACTGGTT-3' (SEQ ID NO:30) are examples of primers designed for the selection of BoGSL-ALK alleles; IPM1, 5'-GCCATCTTCGCACCCAAA-3' (SEQ ID NO:31) and IPM9, 5'-GTAGTATTCT-CAAAATCTTGT-3' (SEQ ID NO:24) exemplify primers designed for the selection of BoGSL-ELONG alleles; and Ce39, 5'-GAATGTCCTAAAATCAATACT-3' (SEQ ID NO:27); and Ce40, 5'-TTTTCACTAGCGTTCCAATT-3' (SEQ ID NO:28) represent primers useful for the selection of BoGSL-PRO alleles.

The primers find use in identifying the presence or absence of either the functional or non-functional alleles of BoGSL-ALK, BoGSL-PRO and BoGSL-ELONG. For example, primers of the invention are used to identify the introgression of a nonfunctional allele, such as BoGSL-ALK from broccoli or BoGSL-ELONG from cauliflower, into other *Brassica* species. Through introgression of a nonfunctional allele, selected species of *Brassica* crops can be induced to synthesize increased amounts of glucoraphanin or sinigrin, as desired. For instance, with the construction of alien addition lines that contain the two normal diploid genomes of Chinese cabbage (*Brassica rapa*) and additional chromosomes of broccoli (*B. oleracea*), the primers can be used to track the introgression or transfer of a nonfunctional broccoli BoGSL-ALK allele into the *B. rapa* chromosome. (see Quiros, in *DNA-Based Markers in Plants*, (2000) R L Phillips and J K Vasil, eds., Kluwer Acad. Press; McGrath, et al., *Mol. Gen. Genet.* (1990) 223:198; and Quiros, et al., *Theor. Appl. Genet.* (1987)). In this way, it is possible to create a *Brassica* species that synthesizes glucoraphanin or sinigrin or another desired GSL at higher levels.

The primers also find use in the development of open pollinated and/or self-fertile *Brassica* species with specific GSL content. The availability of such self-fertile *Brassica* plants is important for convenient and efficient seed production for the sprout industry and for the development of green manure crops as soil biofumigants. For example, most existing broccoli varieties available today in the market are F1 hybrids. Because of this, broccoli seed is very expensive for use in broccoli sprouts production, precluding wide availability of broccoli sprouts that predictably contain enough glucoraphanin to have anticarcinogenic properties. In the case of broccoli×cauliflower doubled haploids, the primers are used for the efficient selection of self-fertile plants with the desired genotype of BoGSL-PRO+/BoGSL-ELONG−/BoGSL-ALK+ for those that accumulate sinigrin, or BoGSL-PRO−/BoGSL-ELONG+/BoGSL-ALK− for plants that accumulate glucoraphanin.

A nucleic acid encoding an enzyme involved in the biosynthesis and modification of a glucosinolate molecule can be isolated from any of a number of plants, including *Brassica oleracea* subspecies such as broccoli (*Italica* group), cauliflower (*Botrytis* group), cabbage (*Capitata* group), collard (*Viridis* group), brussel sprouts (*Gemmifera* group), kohlrabi (*Gongylodes* group) and the many varieties of kale (*Alboglabra, Costata, Medullosa, Nanofimbriata, Palmifolia, Sabauda, Sabellica* and *Tronchuda* groups). The location and sequences of the genes encoding glucosinolate-modifying enzymes, particularly those involved in the elongation, desaturation, oxidation and hydroxylation of sidechains, can be efficiently identified using any of the several PCR marker systems known in the art, including Random Amplified Polymorphic DNA (RAPD), Simple Sequence Repeat Polymorphism (SSR) and Amplified Fragment Length Polymorphism (AFLP). In addition, Sequence-Related Amplified Polymorphism (SRAP) as described herein can be used.

Nucleic acids encoding desired glucosinolate-modifying enzymes can be identified in a variety ways. For example, a source of a desired gene encoding a glucosinolate-modifying enzyme, such as a genomic, bacterial artificial chromosome (BAC) or yeast artificial chromosome (YAC) library is screened with detectable enzymatically—or chemically—synthesized probes. Oligonucleotide probes also can be used to screen sources and can be based on sequences of known genes that encode glucosinolate modifying enzymes, including sequences conserved among known glucosinolate biosynthesis enzyme genes, or on peptide sequences obtained from a desired purified protein. Oligonucleotide probes based on amino acid sequences can be degenerate to encompass the degeneracy of the genetic code, or can be biased in favor of the preferred codons of the source organism. Probes can be enzymatically synthesized from DNAs of known genes encoding glucosinolate biosynthesis enzymes for high, moderate or reduced-stringency hybridization methods, as desired. For discussions of nucleic acid probe design and annealing conditions, see, for example, Sambrook et al., Molecular Cloning: A Laboratory Manual ($2^{nd}$ or $3^{rd}$ ed.), Vols. 1-3, Cold Spring Harbor Laboratory, (1989 or 2001) or Current Protocols in Molecular Biology, F. Ausubel et al., ed., Greene Publishing and Wiley-Interscience, New York (1987), each of which is incorporated herein by reference. Techniques for manipulation of nucleic acids encoding glucosinolate-modifying enzymes such as subcloning nucleic acid sequences encoding polypeptides into expression vectors, labelling probes, DNA hybridization, and the like are described generally in Sambrook et al., supra. Alternatively, a desired protein can be entirely sequenced and total synthesis of a DNA encoding that polypeptide performed.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. A labeled nucleic acid probe or oligonucleotide is bound, either covalently, through a linker or a chemical bond, or noncovalently, through ionic, van der Waals, electrostatic, or hydrogen bonds to a label such that the presence of the probe may be detected by detecting the presence of the label bound to the probe. By assaying for the presence or absence of the probe, one can detect the presence or absence of the select sequence or subsequence.

Oligonucleotide probes for identifying sequences of enzymes in a plant glucosinolate biosynthesis pathway are designed to selectively or specifically hybridize (by binding, duplexing, or hybridizing) to a particular nucleotide sequence under stringent hybridization conditions when that sequence is present in a complex mixture (e.g., total cellular or library DNA or RNA).

By "stringent hybridization conditions" is intended conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Nucleic acids of the invention also can be identified by the ability to hybridize under stringent conditions to the exemplified sequences disclosed herein. Stringent conditions for this purpose may be achieved with the addition of destabilizing agents such as formamide. For high stringency hybridization, a positive signal is at least two times background, preferably 10 times background hybridization. Exemplary stringent hybridization conditions include: 50% formamide, 5×SSC and 1% SDS incubated at 42° C. or 5×SSC and 1% SDS incubated at 65° C., with a wash in 0.2×SSC and 0.1% SDS at least about 50° C. or 60° C., more usually about 65° C. A positive hybridization is at least twice background. Those of ordinary skill will readily recognize that alternative hybridization and wash conditions can be utilized to provide conditions of similar stringency.

Encompassed by the present invention are related genes encoding enzymes involved in the glucosinolate biosynthesis pathway from the same or other subspecies of *Brassica oleracea*. Such related genes encoding glucosinolate modifying enzymes include variants of the disclosed ORFs that occur naturally within the same or different subspecies of *Brassica oleracea*, as well as homologues of the disclosed genes from other species and evolutionarily related proteins having analogous function and activity. Also included are genes which, although not substantially identical to the *Brassica oleracea* genes encoding enzymes in the glucosinolate biosynthesis pathway, operate in a similar fashion to produce desired glucosinolate compounds. Related glucosinolate modifying genes can be identified by their ability to function substantially the same as the disclosed glucosinolate modifying genes; that is, they can be substituted for corresponding ORFs from *Brassica oleracea* and still effectively produce a desired glucosinolate molecule, such as glucoraphanin or sinigrin. Related glucosinolate modifying genes also can be identified by screening sequence databases for sequences homologous to the disclosed glucosinolate biosynthesis genes, by hybridization of a probe based on the disclosed glucosinolate modifying genes to a library constructed from the source organism, or by RT-PCR using mRNA from the source organism and primers based on the disclosed glucosinolate modifying gene sequences. Thus, the phrase "glucosinolate modifying gene" or "glucosinolate biosynthesis gene" refers not only to the nucleotide sequences disclosed herein, but also to other nucleic acids that are allelic or species variants of these nucleotide sequences.

By "nucleic acid" is intended deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and 8) Cysteine (C), Methionine (M)

(see, e.g., Creighton, *Proteins* (1984)).

It is therefore understood that nonnatural mutations introduced by deliberate mutation using recombinant technology such as single site mutation or by excising short sections of DNA open reading frames coding for glucosinolate biosynthesis enzymes or by substituting new codons or adding new codons are within the scope of the invention. Such minor alterations substantially maintain the immunoidentity of the original expression product and/or its biological activity. The biological properties of the altered glucosinolate biosynthesis enzymes can be determined by expressing the enzymes in an appropriate cell line and by determining the ability of the enzymes to synthesize particular glucosinolate molecules. Particular enzyme modifications considered minor would include substitution of amino acids of similar chemical properties, e.g., glutamic acid for aspartic acid or glutamine for asparagine (supra).

Preferably, the desired nucleic acid is located and identified by employing the SRAP PCR marker system, which finds use in identifying coding regions of interest in any plant. In applying SRAP to the mapping, tagging and sequence identification of nucleic acid sequences encoding enzymes involved in the biosynthesis of a glucosinolate molecule, primer pairs of about 15-21, preferably 17 or 18, nucleotides in length are used that have 5' core sequences and a 3'-end specific codon. The core sequence includes a 5' non-specific sequence that must be different between the primers in each primer pair, and a 3' 4 nucleotide sequence specific to a forward primer and a reverse primer. The core sequence is about 11-16, preferably 13 or 14, nucleotides long and has 5' "filler sequences" of no specific constitution, of about 8-13, preferably 10 to 11, bases, followed by the sequence CCGG in the forward primer and AATT in the reverse primer. The core is followed by three selective nucleotides at the 3' end. In using the primer pairs to amplify by polymerase chain reaction a desired coding region, the annealing temperature is less stringent in the first 1-10, preferably 5 cycles; set at about 30-40° C., preferably 35° C. The remaining 30-40, preferably 35 cycles are run at a more stringent annealing temperature; set at about 40-60° C., preferably 50° C. The amplified DNA fragments are then separated, usually by gel electrophoresis, but other separating techniques well known in the art could also be used (i.e. chromatography, microfluidics) detected by radionuclide, fluorescent or enzymatic labeling. Isolated amplified fragments are sequenced. The sequenced fragments are used in constructing linkage maps, and in making co-dominance determinations, such that a particular coding region of interest is efficiently tagged, localized and identified.

Of particular interest are genes (i.e. genomic DNA) and open reading frames (ORFs) (i.e. complementary DNA (cDNA)) that can be isolated from any subspecies of *Brassica oleracea* that encode enzymes involved in the biosynthesis and modification of glucosinolate molecules, especially GSL-ELONG, GSL-PRO, GSL-ALK, GSL-OXID and GSL-OH. *Brassica oleracea* genes encoding glucosinolate modifying enzymes can be expressed in transgenic plants to effect biosynthesis or increased biosynthesis of desired glucosinolate molecules, such as glucoraphanin and sinigrin. Other DNAs which are substantially identical in sequence to the *Brassica oleracea* genes encoding glucosinolate modifying enzymes, or which encode polypeptides which are substantially similar to glucosinolate biosynthesis enzymes from *Brassica oleracea* can be used, such as those identified from other *Brassica* subspecies (*Brassica napus*, *Brassica campestris*) or from *Arabidopsis* species, or other plants of the order Capparales. By substantially similar or substantially identical in sequence is intended an amino acid sequence or nucleic acid sequence exhibiting at least 60%, 70%, 75%, 80%, 85%, 90% or 95% sequence identity to the DNA sequences of the broccoli or collard GSL-ELONG, GSL-PRO, GSL-ALK or GSL-OH genes or nucleic acid sequences encoding the amino acid sequences for such genes. For polypeptides, the length of comparison sequences generally is at least 16 to 20 amino acids, preferably at least 20 to 35 to 50 amino acids, and most preferably 75-100 amino acids. For nucleic acids, the length of comparison sequences generally is at least 50 nucleotides, preferably at least 60 nucleotides, and more preferably at least 75 nucleotides, and most preferably, at least 110 nucleotides.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to Bo-GSL-ALK nucleic acids and proteins, for example, the BLAST and BLAST 2.0 algorithms and the default parameters discussed below can be used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra).

These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The regions of a glucosinolate biosynthesis gene encoding a polypeptide important for glucosinolate activity can be determined through routine mutagenesis, expression of the resulting mutant polypeptides and determination of their activities. The coding region for the mutants can include deletions, insertions and point mutations, or combinations thereof. A typical functional analysis begins with deletion mutagenesis to determine the N- and C-terminal limits of the protein necessary for function, and then internal deletions, insertions or point mutants are made in the open reading frame to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a glucosinolate biosynthesis gene-encoded polypeptide that are important for activity. A mutated construct is expressed, and the ability of the resulting altered protein to function as a glucosinolate biosynthesis gene is assayed. Such structure-function analysis can determine which regions may be deleted, which regions tolerate insertions, and which point mutations allow the mutant protein to function in substantially the same way as the native glucosinolate biosynthesis gene. All such mutant proteins and nucleotide sequences encoding them are within the scope of the present invention.

For the most part, some or all of the coding sequences for the polypeptides having glucosinolate-modification activity are from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having glucosinolate modifying activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable to the desired host cell. Methods for synthesizing sequences and bringing sequences together are well established in the literature. In vitro mutagenesis and selection, site-directed mutagenesis, or other means can be employed to obtain mutations of naturally occurring glucosinolate biosynthesis enzyme genes to produce a polypeptide having glucosinolate modifying activity in vivo with more desirable physical and kinetic parameters for function in the host cell, such as a longer half-life or a higher rate of production of a desired glucosinolate molecule.

Once the DNA sequences encoding the glucosinolate modifying genes from an organism capable of glucosinolate production have been obtained, they are placed in a vector capable of replication in a host cell, or of being propagated in vitro by means of techniques such as PCR or long PCR. Replicating vectors can include plasmid constructs, phage, viruses, cosmids and the like. Desirable vectors include those useful for mutagenesis of the gene of interest or for expression of the gene of interest in host cells. A glucosinolate synthesis enzyme or a homologous protein can be expressed in a variety of recombinantly engineered cells. Numerous expression systems are available for expression of DNA encoding a glucosinolate modifying enzyme. Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a nucleic acid construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus. To achieve expression in a host cell, the transformed DNA is operably associated with transcriptional and translational initiation and termination regulatory regions that are functional in the host cell.

The expression of natural or synthetic nucleic acids encoding a glucosinolate biosynthesis enzyme of interest is typically achieved by operably linking the DNA to a promoter (which is either constitutive or inducible) within an expression vector. By expression vector is meant a DNA molecule, linear or circular, that comprises at least one expression cassette, each expression cassette comprising a segment encoding a glucosinolate biosynthesis enzyme, operably linked to additional segments that provide for its transcription. A transcriptional cassette for transcription of a nucleotide sequence of interest includes in the direction of transcription, an transcriptional initiation or promoter region and optionally a translational initiation region, a DNA sequence of interest, and a transcriptional and optionally translational termination region functional in a the host cell of interest. When the cassette provides for the transcription and translation of a DNA sequence of interest it is considered an expression cassette. One or more introns may be also be present, and other sequences may also be present, including those encoding transit peptides and secretory leader sequences as desired.

For expression from constructs comprising at least one expression cassette in a transgenic plant genome, the one or more coding regions are provided in either the sense or antisense orientation under the regulatory control of the same or different promoter regions that are heterologous to the coding region. Heterologous promoter regions of use in methods of modifying glucosinolate content in a plant cell include the constitutive CaMV 35S, and the nos, ocs, mas, Mac or DoubleMac, promoters described in U.S. Pat. No. 5,106,739 and by Comai et al., *Plant Mol. Biol.*, 15:373-381 (1990). Inducible promoters, such as the light inducible ribulose-(1,5)-bisphosphate carboxylase/oxygenase (Rubisco) small subunit (SSU) promoter may also find use. The choice of a promoter depends in part upon whether constitutive or inducible expression is desired and whether it is desirable to produce the desired glucosinolate molecules at a particular stage of plant development and/or in a particular tissue or only when the plant or plant cell is exposed to a particular condition. The modifying enzymes can be expressed throughout the plant, or only in particular plant tissues, or only at a particular time depending on the particular intended use for the plant and/or plant parts. Considerations for choosing a specific tissue and/or developmental stage for expression of the ORFs may depend on competing substrates or the ability of the host cell to tolerate expression of a particular glucosinolate compound. Examples of regulatory sequences for targeting expression to a particular location within a host plant such as seed, leaves, fruits, flowers, and roots, are described in U.S. Pat. Nos. 5,463,174, 4,943,674, 5,106,739, 5,175,095, 5,420,034, 5,188,958, and 5,589,379, 5,981,839, 5,530,194, 5,530,185.

Transcriptional and translational initiation and termination regions are derived from a variety of nonexclusive sources, including the DNA to be expressed, genes known or suspected to be capable of expression in the desired system, expression vectors, chemical synthesis. The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. When expressing more than one glucosinolate biosynthesis enzyme ORF in the same cell, appropriate regulatory regions and expression methods should be used. Introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

Generally a marker for selection is contained on the construct to be introduced into the host cell. Alternatively, a separate marker construct can be introduced with the desired construct, as many transformation techniques introduce multiple DNA molecules into host cells. Conveniently, the marker may be resistance to a biocide, particularly an antibiotic, such as kanamycin, G418, bleomycin, hygromycin, chloramphenicol, or the like. The particular marker employed is one which allows for selection of transformed cells as compared to cells lacking the DNA which has been introduced. Selection of a transformed plant or plant cell can occur when the expressed marker protein can be detected, either directly or indirectly. The marker protein can be expressed alone or as a fusion to another protein. The marker protein can be one which is detected by its enzymatic activity; for example β-galactosidase can convert the substrate X-gal to a colored product, and luciferase can convert luciferin to a light-emitting product. The marker protein can be one which is detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Plant cells expressing the marker protein or tag can be selected, for example, visually, or by techniques such as FACS or panning using antibodies.

An expression vector also may include one or more origins of replication, one or more selectable markers, an enhancer, a polyadenylation signal, etc. Expression vectors generally are derived from plasmid or viral DNA, and can contain elements of both. The term "operably linked" indicates that the segments are arranged so that they function in concert for their intended purposes, for example, transcription initiates in the promoter and proceeds through the coding segment to the terminator. See Sambrook et al., supra.

In preparing the constructs, the various DNA fragments may be manipulated, so as to provide for DNA sequences in the proper orientation and, as appropriate, in proper reading frame for expression; adapters or linkers may be employed for joining the DNA fragments or other manipulations may be involved to provide for convenient restriction sites, removal of superfluous DNA, removal of restriction sites, or the like. In vitro mutagenesis, primer repair, restriction, annealing, resection, ligation, or the like may be employed, where insertions, deletions or substitutions, e.g. transitions and transversions, may be involved. Conveniently, a vector or cassette may include a multiple cloning site downstream from the transcription initiation region, so that the construct may be employed for a variety of sequences in an efficient manner. Components of DNA constructs including transcription cassettes of this invention may be prepared from sequences which are native (endogenous) or foreign (exogenous) to the host. By foreign is intended that the sequence is not found in the wild-type host into which the construct is introduced. Heterologous constructs will contain at least one region which is not native to the gene from which the transcription initiation region is derived.

The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell. In vitro expression can be accomplished, for example, by placing the coding region for the glucosinolate modifying enzyme in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for glucosinolate modifying enzymes for example by determining their activity, or the synthesized enzyme can be purified and then assayed.

Methods of modifying the glucosinolate composition of a plant or plant cell of interest are carried out by transforming the plant with one or more constructs that each express at least one nucleic acid that encodes a glucosinolate modifying enzyme. Constructs comprising the glucosinolate biosynthesis enzyme ORFs of interest can be introduced into a host plant cell by any of a variety of standard techniques, depending in part upon the type of host plant cell. These techniques include transfection, infection, biolistic impact, electroporation, microinjection, scraping, protoplast fusion, injection or any other method which introduces the gene of interest into the host plant cell (see U.S. Pat. Nos. 4,743,548, 4,795,855, 5,068,193, 5,188,958, 5,463,174, 5,565,346 and 5,565,347). For convenience, a host plant cell which has been manipulated by any method to take up a DNA sequence or construct is referred to as "transformed" or "recombinant" herein. The subject host plant or plant cell will have at least have one copy of the expression construct and may have two or more, depending upon whether the gene is integrated into the genome, amplified, or is present on an extrachromosomal element having multiple copy numbers.

A preferred method of introduction of constructs into a plant cell host is by transfection employing *A. tumefaciens* or *A. rhizogenes* as the transfecting agent. For transformation with *Agrobacterium*, plasmids can be prepared in *E. coli* which contain DNA homologous with the Ti-plasmid, particularly T-DNA. The plasmid may or may not be capable of replication in *Agrobacterium*, that is, it may or may not have a broad spectrum prokaryotic replication system such as does, for example, pRK290, depending in part upon whether the transcription cassette is to be integrated into the Ti-plasmid or to be retained on an independent plasmid. The *Agrobacterium* host will contain a plasmid having the vir genes necessary for transfer of the T-DNA to the plant cell and may or may not have the complete TDNA. At least the right border and frequently both the right and left borders of the T-DNA of the Ti- or Ri-plasmids are joined as flanking regions to the transcription construct. The use of T-DNA for transformation of plant cells has received extensive study and is amply described in EPA Ser. No. 120,516, Hoekema, In: The Binary Plant Vector System Offset-drukkerij Kanters B. V., Alblasserdam, 1985, Chapter V, Knauf, et al., Genetic Analysis of Host Range Expression by *Agrobacterium*, In: Molecular Genetics of the Bacteria-Plant Interaction, Puhler, A. ed., Springer-Verlag, NY, 1983, p. 245, and An et al., *EMBO J.*, 4:277-284 (1985). Transgenic plant cells are then placed in an appropriate selective medium for selection of transgenic cells which are then grown to callus, shoots grown and plantlets generated from the shoot by growing in rooting medium.

The choice of a host plant cell is influenced in part by the desired glucosinolate profile of the transgenic plant cell, and the native profile of the host plant cell. Even where the host plant cell expresses glucosinolate modifying gene activity for one or more glucosinolate molecules, expression of heterologous sequences encoding glucosinolate synthesis enzymes can provide for production of novel glucosinolate molecules not natively produced by the host plant cell. Any type of plant cell can be used for host cells, including dicotyledonous plants, monocotyledonous plants, and cereals. Of particular interest are crop plants such as *Brassica*, especially *Brassica oleracea* plants including broccoli, cauliflower, cabbage, collard, brussel sprouts, and the many varieties of kale, but also *Brassica napus* and *Brassica campestris* (also known as *Brassica rapa*). Other plants of interest include those of the order Capparales, particularly *Arabidopsis*, and other crop plants, such as tobacco, soybean, corn, and the like.

The methods can be carried out with the intent of increasing or decreasing a particular attribute of the glucosinolate composition in a plant, such as producing increased or decreased amounts of methylsulfinylalkyl, alkenyl or hydroxy-type glucosinolate molecules or with the intent of increasing or decreasing the amount of a desired glusosinolate molecule, such as increasing the amounts of glucoraphanin or sinigrin or decreasing the amounts of progoitrin, as compared to non-transformed or non-transgenic plants. Several methods can be employed. Additional genes encoding the glucosinolate enzymes of interest can be introduced into the host plant. For production of desired glucosinolate molecules, depending upon the host plant cell, one or more nucleic acid sequences encoding enzymes that catalyze distinct reactions in the glucosinolate biosynthesis pathways are introduced as tandemly expressed coding sequences separated by an internal ribosome entry site in a single expression cassette, or as part of individual expression cassettes, wherein each expression cassette is introduced on a single DNA vector or on multiple DNA vectors into a host cell. Thus, the transformed host plant will have at least one copy of the expression construct and may have two or more, depending upon whether the gene is integrated into the genome, amplified, or is present on an extrachromosomal element having multiple copy numbers.

Methods encompassed by the present invention include increasing or decreasing the length, desaturation and hydroxylation of the glucosinolate content in a plant or plant cell in comparison to a non-transformed plant or plant cell. The desired end result is achieved by transforming a plant with nucleic acid encoding one or more enzymes from a glucosinolate biosynthesis pathway. The gene can be expressed in either the sense or antisense orientation depending upon the desired outcome. The gene is placed in the sense orientation to enhance production of the catalytic product and in the antisense orientation to inhibit production of the catalytic product. As desired, the relative amounts of particular glucosinolate molecules, such as glucoibeverin, glucoerucin, glucoiberin, glucoraphanin, sinigrin, gluconapin and progoitrin can be increased or decreased. For the production or modification of glucosinolate compounds in plants, genes encoding enzymes involved in the synthesis of glucosinolates, such as the GSL-ELONG, GSL-PRO, GSL-ALK, GSL-OXID and GSL-OH are used. When it is necessary to use multiple gene constructs to achieve a desired result, for example plants expressing both a GSL-ELONG gene in the sense orientation and a GSL-ALK gene in the antisense orientation, the plants may be obtained by co-transformation with two constructs, or with one construct comprising expression cassettes for the two coding regions, or by transformation with individual constructs followed by traditional plant breeding methods to obtain plants expressing both of the desired genes. For example, where less than all glucosinolate modifying genes required for glucosinolate biosynthesis have been inserted into a single plant, plants containing a complementing gene or genes can be crossed to obtain plants containing a full complement of glucosinolate modifying genes to synthesize a desired glucosinolate compound. Traditional breeding techniques are also used when a construct is introduced into a hybrid species of plant (e.g., a cauliflower×broccoli hybrid) and it is desired to have the transgenic gene in a plant having the genetic character of either parent plant. In this way, a transgenic gene encoding a glucosinolate biosynthesis modification enzyme ultimately can be introduced into a plant by either transgenic or conventional breeding methods.

Expression from a native glucosinolate modifying enzyme gene locus also can be increased or decreased through homologous recombination, for example by inserting a stronger or weaker promoter into the host genome to cause increased or decreased expression, by removing or adding destabilizing or stabilizing sequences from either the mRNA or the encoded protein, or by deleting that information from the host genome (see U.S. Pat. No. 4,910,141 and U.S. Pat. No. 5,500,365).

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay, HPLC analysis of extracted glucosinolate products, or visual inspection. As shown in the examples that follow, glucosinolate profiles are conveniently assessed using HPLC. To carry out an HPLC analysis, leaves of plants to be tested are crushed and extracted using an organic solvent. Glucosinolates are desulfated before separation over an HPLC column. The HPLC chromatogram of a test glucosinolate composition is then compared to the chromatogram of a known desulfoglucosinolate composition used as a standard. The presence or absence of particular glucosinolate species is then identified by comparison of the HPLC chromatograms.

Once transgenic plants have been obtained, they may be grown into adult plants having the desired phenotype. The seeds from adult plants may serve as a source for growing additional plants having the desired characteristics. The terms transgenic plants and transgenic cells include plants and cells derived from either transgenic plants or transgenic cells.

The uses of the subject nucleic acid sequences are several. Probes based on the DNAs of the present invention find use in methods for isolating related molecules or in methods to detect additional organisms expressing glucosinolate modifying genes. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practicable to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of a probe to a target via isothermal titration calorimetry, or by coating the probe or target on a surface and detecting the change in scattering of light from the surface produced by binding of a target or a probe, respectively, is done with the BIAcore system.

Glucosinolate compounds produced by recombinant means find applications in a wide variety of areas. In the present case, recombinant expression of glucosinolate modifying genes, or antisense glucosinolate biosynthesis gene transcripts, can alter the levels of specific glucosinolate molecules or several glucosinolate molecules within a single pathway, or derivatives thereof, found in plant parts and/or plant tissues. In doing so, the nutritional value and anticarcinogenic of the properties of the plant, particularly an edible plant, are enhanced. A glucosinolate modifying enzyme gene polypeptide coding region is expressed either by itself or with other genes, especially those that encode other glucosinolate modifying enzymes, in order to produce tissues and/or plant parts containing higher proportions of desired glucosinolate molecules or containing a glucosinolate composition with enhanced nutritional value and anti-carcinogenic properties than does the unmodified tissues and/or plant parts. Additionally, naturally pest resistant plants can be obtained for example by expression of sinigrin to protect a plant and/or plant parts from fungi and nematodes.

The following examples are offered by way of illustration of the present invention, not limitation.

EXAMPLES

Example 1

Identification by Genetic Analysis of the Major Genes Involved in the Glucosinolate Pathway in *Brassica oleracea*

HPLC analysis of glucosinolates was performed on four populations of *Brassica oleracea* crops, including 89 recombinant inbred (RI) lines of collard×cauliflower, 52 RI lines of collard×broccoli, 88 F2 plants of collard×broccoli, and 643 cauliflower×broccoli. After comparison of the aliphatic glucosinolate profiles of individual plants in each line, the presence of three genes was inferred: 1) BoGsl-alk, controlling side-chain desaturation and segregating in three populations; 2) BoGsl-elong/BoGsl-pro, controlling the synthesis of 3-carbon side-chain glucosinolates, such as glucoiberin and sinigrin, and segregating in the collard×broccoli RI population and the two F2 populations; 3) BoGsl-elong determining 4-carbon glucosinolates, like glucoraphanin, progoitrin, only segregating in the cauliflower×broccoli F2 population. The results indicate that the synthesis of 3-carbon and 4-carbon side-chain glucosinolates is controlled by independent genes. Further, the genes controlling side-chain desaturation and hydroxylation can act on both 3-carbon (3C) and 4-carbon (4C) side chains (Table 1).

According to the present model, the 3C, 4C, and 5C GSL are closely related biosynthetically because all of them originate from the same precursor, methionine. In this model, it is expected that the presence of the dominant (plus) allele for the Gsl-elong gene results in 4C GSL, whereas presence of the dominant allele for Gsl-pro results in 3C GSL. Similarly, a dominant allele for BoGSL-ALK results in synthesis of alkenyl glucosinolates, such as sinigrin (3C) and gluconapin (4C), which can be converted by hydroxylation into the anti-nutrient progoitrin (FIG. 1), whereas the recessive (minus) allele BoGSL-ALK results in the accumulation of glucoraphanin (4C), a source for the anticarcinogen sulfurophane, and glucoiberin (3C) (Li et al., *J. Amer. Soc. Hortic Sci*, 126(4):427 (2001)).

TABLE 1

Genetic analysis of three major glucosinolate genes in four segregating populations

| Inferred Genotype | Collard × cauliflower (RI) | Collard × broccoli (RI) | Collard × broccoli (F2) | Broccoli × cauliflower (F2) |
| --- | --- | --- | --- | --- |
| PRO−/ELONG−/ALK− | | | | 35 (40.2)[a] |
| PRO+/ELONG−/ALK− | | | | 134 (120.6) |
| PRO+/ELONG−/ALK+ | | | | |
| PRO−/ELONG+/ALK− | | 14 (13) | 5 (5.5) | 137 (120.6) |
| PRO−/ELONG+/ALK+ | | 8 (13) | 18 (16.5) | |
| PRO+/ELONG+/ALK− | 36 (44.5) | 13 (13) | 17 (16.5) | 337 (361.8) |

TABLE 1-continued

Genetic analysis of three major glucosinolate genes in four segregating populations

| Inferred Genotype | Collard × cauliflower (RI) | Collard × broccoli (RI) | Collard × broccoli (F2) | Broccoli × cauliflower (F2) |
| --- | --- | --- | --- | --- |
| PRO+/ELONG+/ALK+ | 53 (44.5) | 17 (13) | | 48 (49.5) |

[a]expected values in parenthesis (number of individual plants)

Example 2

Mapping the BoGSL-ALK gene using Sequence-Related Amplified Polymorphism (SRAP)

In order to clone the genes inferred above, a simplified high throughput marker system called Sequence-Related Amplified Polymorphism (SRAP) was used, as described by Li and Quiros in *Theoretical and Applied Genetics*, 103: 455-461 (2001), incorporated herein by reference.

Materials and Methods

Plant Material

The SRAP marker system was developed primarily for *Brassica* species, but is also useful in other crops such as potato, rice, apple, citrus, cherry, plum, garlic, lettuce and celery.

The following *B. oleracea* crops were included in the study: broccoli, cauliflower, and kale. A population of recombinant inbred (RI) lines resulting from crossing collard×cauliflower was used for mapping the GSL-ALK gene and sequencing some of the markers. A doubled haploid (DH) population of broccoli and cauliflower was also used to test the reproducibility of the SRAP markers. For cDNA fingerprinting, Chinese cabbage was used as a source of mRNA from isolated pollen mother cells, meiocytes and meiotic flower buds.

DNA Extraction

A modified version of the CTAB method was used to extract genomic DNA. A 1.5 ml tube containing approximately 0.3 g of fresh leaf tissue was placed into liquid nitrogen for 30 sec and its contents crushed with a small plastic bar. 0.5 ml 2×CTAB buffer was added to the tubes and incubated at 65° C. for 90 min. After incubation, 0.4 ml chloroform was added and the tubes were centrifuged at 14,000 rpm for 3 min. The supernatant was transferred into a new tube and the DNA precipitated in a 0.6 volume of 2-propanol. The DNA was then washed with 70% ethanol and dissolved in TE buffer.

Protocol for SRAP Marker System

SRAP is a PCR-based marker system of two primers, a forward primer of 17 bases and a reverse primer of 18 bases. These are labeled with [γ33P]-ATP for amplification of genomic DNA.

The forward primers consist of a core sequence of 14 bases. The first 10 bases starting at the 5' end are "filler" sequences of no specific constitution, followed by the sequence CCGG and then by three selective nucleotides at the 3' end. Variation in these three selective nucleotides generates a set of primers sharing the same core sequence. The reverse primers consist of the same components as the forward primers with the following variations: The filler is followed by AATT instead of the CCGG sequence. Following the AATT sequence, three selective bases are added to the 3' end of the primer. Preferably, the forward and reverse primers do not form hairpins or other secondary structures, and have a GC content of 40-50%. Further the filler sequences of the forward and reverse primers must be different from each other and can be 10 or 11 bases long.

Examples of Forward Primers:

```
me1,   5'-TGAGTCCAAACCGGATA-3',   (SEQ ID NO:6)
me2,   5'-TGAGTCCAAACCGGAGC-3',   (SEQ ID NO:7)
me3,   5'-TGAGTCCAAACCGGAAT-3',   (SEQ ID NO:8)
me4,   5'-TGAGTCCAAACCGGACC-3',   (SEQ ID NO:9)
me5,   5'-TGAGTCCAAACCGGAAG-3'.   (SEQ ID NO:10)
```

Examples of Reverse Primers:

```
em1,   5'-GACTGCGTACGAATTAAT-3',   (SEQ ID NO:11)
em2,   5'-GACTGCGTACGAATTTGC-3',   (SEQ ID NO:12)
em3,   5'-GACTGCGTACGAATTGAC-3',   (SEQ ID NO:13)
em4,   5'-GACTGCGTACGAATTTGA-3',   (SEQ ID NO:14)
em5,   5'-GACTGCGTACGAATTAAC-3',   (SEQ ID NO:15)
em6,   5'-GACTGCGTACGAATTGCA-3'.   (SEQ ID NO:16)
```

DNA Amplification

The first five cycles are run at 94° C., 1 min, 35° C., 1 min, and 72° C., 1 min for denaturing, annealing and extension, respectively. Then the annealing temperature is raised to 50° C. for another 35 cycles. For amplification we used the cocktail used in other routine PCR marker applications (Vos et al., *Nucleic Acids. Res.*, 23:4407-4414 (1995)). The amplicons are separated by denaturing acrylamide gels and detected by autoradiography.

AFLP Protocol.

The AFLP procedure was performed according to Vos et al., (1995) supra. The sequences of all adapters and primers were the same as those in the original protocol. The oligonucleotides for the adapters and primers were commercially synthesized (Integrated DNA Technologies, Inc, USA). The adapters were produced by using similar molecular concentrations of the two complementary oligonucleotides for each adapter, denaturing the DNA for 5 min at 94° C., followed by annealing by decreasing the temperature to 24° C. slowly (1° C. in 2 min). All restriction enzymes, T4 DNA Ligase, and T4 polynucleotide kinase were obtained from New England Biolabs Inc. EcoRI and TaqI adapters were used (instead of MseI and EcoRI to avoid possible marker clustering), and a two-steps digestion was performed. First, the genomic DNA was digested by EcoRI in TaqI buffer at 37° C., then TaqI was added and the tubes incubated for 3 h at 65° C. The ligation, primer, labeling, two-step PCR, and gel analysis were the same as in the original protocol.

Sequencing of SRAP Marker Bands

Only bands from *Brassica* species were sequenced. We developed the following protocol to isolate DNA from the SRAP gels for direct sequencing. Denaturing, thick polyacrylamide gels (size 35×43 cm, thickness, 0.8 mm) were poured using double spacers (0.4 mm each) to run the amplified DNAs. In these thick gels, 20 µl of sample can be loaded in each well, which made it easy to collect enough DNA from a single band for direct sequencing. After electrophoresis, the gel was exposed overnight to a high sensitivity film, (Kodak BioMax). Using the exposed film as a blueprint, the gel pieces containing the polymorphic bands were cut and introduced into a dialysis tube. The dialysis tube was placed into the buffer tank of a sequencing gel apparatus, and the DNA was electroeluted in 1×TBE buffer (Fisher FB-SEQ 3545). Application of 2000 volts, which is the same voltage used for running sequencing gels, resulted in the complete electroelution of DNA into buffer from the gel fragment. After ethanol precipitation and TE buffer suspension, the DNA was used for direct sequencing. The sequencing was accomplished using an ABI377 sequencer (Perkin-Elmer Company).

Marker Scoring and Mapping

Sixteen primer pairs for SRAP and 20 primer pairs for AFLP were used to generate the map. Each polymorphic band was scored as a single dominant marker. Data were analyzed with Mapmaker version 2.0 for Macintosh (Lander et al., *Genomics*, 1:174-181 (1987)). A minimum LOD score of 3.0 was used for map construction.

Glucosinolate Analysis.

Analysis of glucosinolates was performed with the protocol based on Kraling et al., *Plant Breed*, 105:33-39 (1990)), which was modified for leaf extraction (instead of seeds). For this purpose we ground approximately 2 g of fresh leaves collected from 6 week-old seedlings in liquid nitrogen. The tissue was extracted twice with 70% methanol at 80° C. for 10 min. After applying the supernatant to a DEAE-Sephadex A-25 (Sigma) column, the glucosinolates were converted into desulfoglucosinolates with sulfatase (0.5% enzyme in water for 12 h at room temperature, Sigma H-I type). The desulfoglucosinolates were then eluted by adding 1.5 ml water. The resulting mixture was separated by HPLC (Shimadzu) using a Lichrospher 100 RP-18 column (Alltech Associates, Inc. USA) and a linear solvent gradient from 1% to 19% acetonitrile in water over 20 min. The flow rate was 1.5 ml/min at 32° C. The HPLC chromatogram was compared to the desulfoglucosinolate profile of "Linetta", a rapeseed variety widely used as a standard for glucosinolate identification to compare the peaks with the corresponding glucosinolates. The presence of desulfosinigrin and desulfoglucoraphanin peaks was confirmed by using pure authentic sinigrin (Sigma) as an internal standard. Glucosinolate content was quantified with glucotropaeolin (Merck Co.) as an internal standard.

Results and Discussion

Principles of the Method

Number of Primers and Primer Sizes: The optimal SRAP primer size is between 17 and 18 bp. Primer size and the use of a two-primer combination are essential to successfully amplify SRAP bands.

PCR Conditions: The initial annealing temperature for the first five cycles was set at 35° C. The rationale behind using this temperature is based on the fact that primer annealing to the DNA template depends on the matching level of both sequences, and amplification efficiency is determined by the effectiveness of the primer binding. The low initial annealing temperature assures the binding of both primers to sites of partial match in the target DNA. The annealing temperature was then increased for the subsequent 35 cycles to 50° C. This temperature change assures that the DNA products amplified in the first five cycles were efficiently and consistently amplified in exponential fashion during the rest of the cycles. When the annealing temperature was kept at 35° C. for all 40 cycles bands of poor reproducibility resulted.

Primer Sequence: The purpose for using the "CCGG" sequence in the core of the first set of the SRAP primers was to target exons of open reading frame (ORF) regions. This rationale is based on the fact that exons are normally in GC-rich regions. For example, in completed sequences of chromosomes 2 and 4 of *Arabidopsis thaliana*, the GC content of the exons is 43.6% and 44.08%, respectively. In introns, these values drop to 32.1% and 33.08%, respectively (Lin et al., *Nature*, 402:761-767 (1999); The EU *Arabidopsis* Genome, *Nature*, 391:485-488 (1999)). Additionally, genes are nearly evenly distributed along these two chromosomes, except within the centromeric region, where less gene density is evident (Copenhaver et al., *Science*, 286:2468-2474 (1999)). Based on this observation, we randomly selected 20 BACs from the Genbank database and checked their sequences. Approximately 66% of the sequence CCGG motif occur in exons in these clones. Since exons account for approximately one third of the genome contained in chromosomes 2 and 4, (Lin et al., (1999) supra; The EU *Arabidopsis* Genome, (1999) supra) by using the CCGG primer set, we hoped to preferentially amplify sequences containing these elements. However, since exonic sequences are generally conserved among different individuals (Quiros et al., *Genetics*, 157:1321-1330 (2001)), their low level of polymorphism precludes using them as sources of markers. To counteract this potential problem, we designed the second primer set with a core containing the AATT sequence near the 3' end to target AT-rich regions. Normally these are found more frequently on promoters and introns (Lin et al., (1999) supra; The EU *Arabidopsis* Genome, (1999) supra). Since introns, promoters and spacers are usually variable among different individuals, this intrinsic dissimilarity makes it feasible to generate polymorphic bands based on introns and exons.

Reproducibility, Polymorphism and Genome Coverage

Using the same primer combination, we amplified DNA from different *B. oleracea* crops, including cauliflower, collard, and broccoli. A single primer combination detected more than 10 polymorphic bands per individual. Although most polymorphic bands maintained similar profiles for different populations of these crops, some of them were crop specific. Different crops shared a few monomorphic bands (data not shown). The polymorphic bands were fully reproducible when the same DNA samples were run in independent experiments.

Map Construction: To demonstrate that SRAP markers have a good coverage of the genome, which was anticipated because of targeting ORFs, a genetic map was constructed using the RI lines. The map constructed in the 86 RI lines of collard×cauliflower consisted of 130 SRAP and 120 AFLP markers, plus the GSL-ALK gene. All AFLP markers were dominant, whereas approximately 20% of the polymorphic SRAPs (26 markers) segregated as co-dominant markers. The AFLP as well as SRAP markers were distributed fairly evenly in nine major linkage groups covering 2165 cM (Table 2). No major differences of genome coverage were observed for the two marker techniques. Therefore, similarly to AFLPs, the wide genome coverage of SRAP markers and their high reproducibility results in the construction of genetic maps with optimal marker distribution.

TABLE 2

Distribution of SRAP and AFLP markers in 9 linkage groups (L1-L9) of *B. oleracea*

|  | L1 | L2 | L3 | L4 | L5 | L6 | L7 | L8 | L9 |
|---|---|---|---|---|---|---|---|---|---|
| SRAP | 26 | 23 | 21 | 9 | 14 | 16 | 13 | 12 | 6 |
| AFLP | 23 | 21 | 21 | 7 | 16 | 8 | 7 | 13 | 4 |

As expected, each co-dominant markers pair (each band was scored independently), landed in the map at almost the same position, at distances between 2 to 10 cM. They failed to fall exactly at the same location because, being scored separately, their genetic distance theoretically matched the level of residual heterozygosity ($1/2^5$), which exists in this RI population after five rounds of selfing. The relatively high frequency of co-dominant SRAP markers is another important advantage of this technique as compared to using AFLP markers.

Tagging the BoGSL-ALK Gene: Presence of specific aliphatic glucosinolates in the RI population and its parental lines allowed the follow up of the segregation and tagging of the BoGSL-ALK gene. Similarly to their cauliflower parent, 36 of the RI lines contained only glucoiberin and glucoraphanin, thus indicating that they had the homozygous recessive genotype for the desaturation allele GSL-ALK⁻ (Mithen et al., *Heredity*, 74:210-215 (1995)). The collard parent as well as the rest of the 56 lines contained glucoiberin, glucoraphanin, sinigrin and progoitrin. Therefore these had the GSL-ALK⁺ dominant allele. The observed segregation did not deviate significantly from the expected 1:1 Mendelian ratio for a monogenic trait ($X^2=0.14$). BoGSL-ALK mapped on L1 linkage group at 1.4 cM from marker SRAP 133. This distance however is overestimated by the residual heterozygosity of the mapping population, and by the scoring of the markers as dominant markers. Sequencing disclosed that SRAP133 had a size of 259 bp, and interestingly, it matched the sequence of an open reading frame for a putative gene on *Arabidopsis* BAC clone F4C21 (Table 2). This gene is located on chromosome IV, in the same position where Mithen et al., (1995) supra) mapped a desaturation gene. Thus the SRAP133 is inside this gene and the functional genes for the desaturation of glucosinolates, in *B. oleracea* and in *Arabidopsis* are very similar.

Direct Sequencing of SRAP Markers.

The ability to sequence from complex profiles a specific marker tagging a given trait is important for marker-assisted selection. Marker-based selection permits the rapid screening of large size segregating populations. Sequence information is useful to permit the conversion of dominant to co-dominant markers. Because most SRAP markers produce clear high-intensity bands rarely overlapping, it is easier than for AFLP markers to sequence them by cutting them directly from the gels. We isolated 29 polymorphic bands resulting from the amplification of the *Brassica* RI lines, using seven different primer combinations. Twenty-five of the 29 sequences could be read to completion; four bands could be only partially read and these were not analyzed. It was found that the GC content of 16 (64%) of the sequences was over 35%, which indicates that they possibly fall into exons, assuming similar gene structures in *Brassica* and *Arabidopsis* (Quiros et al., *Genetics*, 157:1321-1330 (2001); Lin, (1999) supra). After a BLAST search, it was found that 15 (60%) shared significant similarity to reported gene sequences stored in the Genbank database (Table 3). This finding confirmed that indeed a large proportion of the bands generated by SRAPs include exons in ORFs, which are expected to be evenly distributed along all chromosomes.

aimed to clone genes expressing specifically in pollen mother cells. We found tissue-specific bands, which likely correspond to genes expressed specifically in those tissues.

TABLE 3

Analysis of a sample of SRAP sequences isolated from acrylamide gels.

| Marker name[a] | Primers | size (bp) | GC (%) | BLASTn or x Score (bits)[b] | Genbank Accession number |
|---|---|---|---|---|---|
| SRAP1 | em1 + me1 | 299 | 33.4 | | |
| SRAP2a | em1 + me1 | 179 | 30.7 | | |
| SRAP2b | em1 + me1 | 170 | 30.6 | | |
| SRAP3 | em1 + me1 | 137 | 32.8 | | |
| SRAP24 | em1 + me4 | 331 | 23.4 | | |
| SRAP29a | em1 + me4 | 125 | 39.0 | | |
| SRAP29b | em1 + me4 | 121 | 38.8 | | |
| SRAP34 | em1 + me5 | 193 | 51.0 | 28.6 (Tx) | Sp/P13730/SGS3 |
| SRAP35 | em1 + me5 | 161 | 26.1 | | |
| SRAP36 | em1 + me5 | 142 | 35.9 | | |
| SRAP37 | em1 + me5 | 390 | 31.5 | 40.2 (Tx) | Gb/AAD24846.1/AC007071 |
| SRAP41 | em2 + me1 | 170 | 42.9 | 44.5 (Tx) | Gb/AAD25847.1/AC006951 |
| SRAP42a | em2 + me1 | 269 | 37.1 | 115 (Tn) | Gb/AC101793.3/AC101793 |
| SRAP42b | em2 + me1 | 237 | 39.7 | 101 (Tn) | Gb/AC101793.3/AC101793 |
| SRAP45 | em2 + me1 | 158 | 49.4 | 55.0 (Tx) | Pir//T01961 |
| SRAP49 | em2 + me2 | 474 | 38.4 | 337 (Tn) | Gb/AF079998.1/AF079998 |
| SRAP50 | em2 + me2 | 454 | 40.5 | 67.9 (Tn) | Gb/AC011000.3/F16P17 |
| SRAP51a | em2 + me2 | 227 | 44.8 | 30.5 (Tx) | Pir//T10241 |
| SRAP51b | em2 + me2 | 217 | 45.4 | 30.5 (Tx) | Pir//T10241 |
| SRAP52 | em2 + me2 | 188 | 25.5 | | |
| SRAP56 | em2 + me3 | 402 | 41.8 | 113 (Tn) | Gb/AC025290.3/F9P14 |
| SRAP59a | em2 + me3 | 293 | 35.8 | 29.3 (Tn) | Ref/NP-006628 |
| SRAP59b | em2 + me3 | 258 | 35.9 | 29.3 (Tn) | Ref/NP-006628 |
| SRA58 | em2 + me3 | 203 | 37.4 | 218 (Tn) | Dbj/AP000423.1/AP000423 |
| SRAP133 | em6 + me1 | 276 | 38.4 | 91.7 (Tn) | GbAC005275.1/AC005275 |

[a]Bands sharing the same number followed by letters a or b are co-dominant bands
[b]BLAST search of Genbank database with program BLASTn or BLASTx. All nine Tn matches fall into exons of *Arabidopsis* sequences Sequencing demonstrated also that SRAP polymorphism results from two events, fragment size changes due to insertions and deletions, which could lead to co-dominant markers, and nucleotide changes leading to dominant markers. Among the sequenced bands we selected five pairs that appeared to be co-dominant in the gel. Sequencing of both parental bands demonstrated similar sequences differing only by small insertions or deletions. The difference in size for each pair of co-dominant markers determined by sequencing, matched the sizes estimated on the gel by migration distance. Therefore, the co-dominant markers resulted from size change delimited by the binding sites of the two primers. The rest of the sequenced SRAP markers were dominant, probably resulting from nucleotide substitutions affecting primer-binding sites.

Other Applications

We used the SRAP protocol to amplify DNA from other crops. These crops were potato rice, lettuce, rapeseed (*B. napus*), garlic, apple citrus, and celery. Among these crops we could get good amplification and easily find polymorphism. In three of these crops, Chinese cabbage (Li and Quiros, unpublished), rapeseed (Riaz et al., *Plant Breeding*, 120:1-5) and celery (Ruiz et al. submitted) we have found markers for a male sterility gene, a cms fertility restorer gene and a virus resistance gene, respectively.

In order to determine the feasibility to use SRAPs for cDNA fingerprinting, we have amplified cDNA isolated from different tissues of *B. rapa* generated in another study Therefore SRAP can be also used to fingerprint cDNAs.

The SRAP marker system is a simple and efficient marker system that can be adapted to a variety of purposes in different crops, including map construction; gene tagging, genomic and cDNA fingerprinting and map based cloning. It has several advantages over other systems: simplicity, reasonable throughput rate, discloses numerous co-dominant markers, allows easy isolation of bands for sequencing and most importantly, it targets ORFs.

Example 3

Expression of the BoGSL-ALK Gene in *Arabidosis thaliana*

Figure 3:
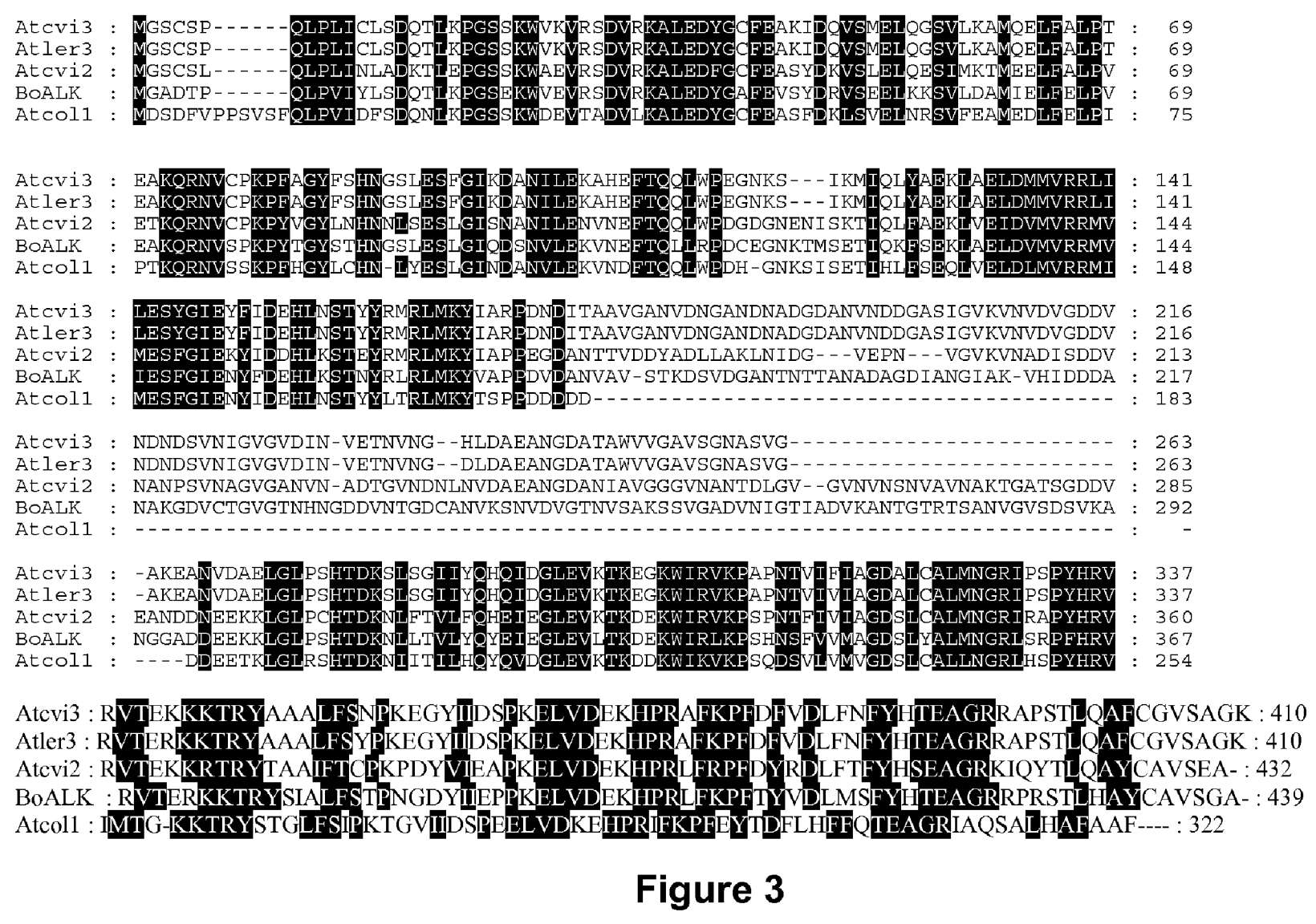

Primers em6-me1 [em6, 5'-GACTGCGTACGAAT-TGCA-3' (SEQ ID NO:16); me1, 5'-TGAGTCCAAACCG-GATA-3' (SEQ ID NO:6) (Li and Quiros, 2001, supra) were used to identify the SRAP 133 marker linked to BoGSL-ALK. Marker SRAP133 was sequenced and primers FC1 and FC2 [FC1, 5 ' GTCAAGGGCAGGTAAGAACAA 3' (SEQ ID NO:17); FC2, 5' GCATTGACGGTTACCTTGAT 3' (SEQ ID NO:18)] were constructed based on this sequence. Then primers FC1-FC2 were used to screen a broccoli BAC library to identify clone B21H13 as one possibly harboring the candidate gene BoGSL-ALK. Among several sequences on this clone with homology to *A. thaliana*, (Quiros et al. 2000 *Brassica* 2000, 3rd ISHS Intl. Symp. on *Brassicas*. 5-9 Sep. 2000) (FIG. 3) a fragment corresponding to the 2-ODD genes of *Arabidopsis* (Hall et al., (2001) supra) was found and subcloned. The sequence of this fragment consisted of 2939 bases (SEQ ID NO:1) with approximate identity of its coding region of 80% to *Arabi-*

*dopsis* ODD-2 gene on BAC clone T419. This fragment from broccoli was considered a candidate gene for BoGSL-ALK. It has three exons and the 5' region of this gene has the expected transcription signals normally observed in functional gene promoters.

Comparative sequence analysis of the structural differences in the functional collard and non-functional broccoli BoGSL-ALK alleles detected three exons in BoGSL-ALK+, resulting in a predicted coding sequence of 1317 nucleotides and a protein of 439 amino acids. The non-functional allele, BoGSL-ALK−, has only two exons with 957 nucleotides of predicted coding sequence, encoding a protein of 319 amino acids. After ClustalW (Thompson, et al. (1994) *Nucleic Acids Res* 22:4673) alignment of genomic DNA sequences for these two alleles, we observed a 2-bp deletion in exon 2 in allele BoGSL-ALK− causing a frameshift that results in the observed shorter coding sequence. We also sequenced the region corresponding to exon 2 in Chinese cabbage (*B. rapa*), a related species of *B. oleracea*, in which GSL-ALK is functional, judged by the existence of alkenyl GSL in this crop. The sequence of Chinese cabbage did not have the small deletion observed in BoGSL-ALK− and had virtually the same sequence as that observed in the functional collard allele BoGSL-ALK+.

It is expected that a dominant (plus) allele for BoGSL-ALK results in synthesis of alkenyl glucosinolates, such as sinigrin (3C) and gluconapin (4C), which can be converted by hydroxylation into the anti-nutrient progoitrin (FIG. 1). On the other hand, the recessive (minus) allele BoGSL-ALK results in the accumulation of glucoraphanin (4C), a source for the anticarcinogen sulfurophane, and glucoiberin (3C) (Li et al., *J. Amer. Soc. Horticult. Sci., (*2001)). The genotype for BoGSL-ALK in the broccoli line used to construct the library is recessive, since this plant accumulates glucoraphanin. In order to demonstrate that the candidate gene identified in the BAC clone was BoGSL-ALK, we constructed primers ODD48-ODD49 (ODD48, 5'TTCCATCATT-TACTTTCTCAG3' (SEQ ID NO:19); ODD49, 5'AAGC-CGGTCCTAATTTGTAA3' (SEQ ID NO:20)) based on the sequence of the candidate gene and amplified the dominant allele from this gene in a collard variety containing gluconapin and progoitrin (SEQ ID NO:2). These alkenyl glucosinolates result by desaturation of glucoraphanin. The resulting amplicons were cloned using a Topo TA cloning kit from Invitrogen Corp. Then the gene was introduced into the transformation binary vector pCB3O2 (Xiang et al., *Plant Mol. Bio.*, 40:711-717 (1999)) for plant transformation using *A. tumefaciens* strain GV3 101. These constructs were used to transform *A. thaliana* Columbia (it has [3C] and glucoraphanin [4C]), and a wild type WS ecotype (it has glucoiberin but not 4C glucosinolates). These two strains have the recessive genotype for GSL-ALK, as judged by the absence of alkenyl glucosinolates in their HPLC profiles.

We screened 200 putative transformants using PCR for the presence of a 520 bp band corresponding to a portion of the vector and the exon 1 of BoGSL-ALK+ allele. All transformed plants generated a band of the expected size, whereas no such band was amplified from untransformed control plants of the *Arabidopsis* wild type ecotype. To investigate BoGSL-ALK expression, we used a pair of primers located inside the collard BoGSL-ALK+ allele to amplify cDNAs generated by the same putative allele introduced to the *Arabidopsis* transformants, using as control untransformed wild type individuals. Positive bands of the expected size (840 bp) were obtained from only transformed plants. These bands were further confirmed to correspond to the BoGSL-ALK+ by collecting DNA from the gels and then sequencing them. Sequencing confirmed that the cDNA sequence from the *Arabidopsis* transformants was identical to the collard cDNA sequence. This test established that the ODD2 *Brassica* homolog from collard expressed in the *Arabidopsis* transformants.

As final confirmation we did functional analysis of the *Arabidopsis* transformants by inspection of their GSL phenotype. In order to avoid possible uncertain changes for GSL in the transformants, due to transient expression or loss of expression of the foreign gene, we used T3 lines subjected to two cycles of selfing to perform the GSL analysis (Kraling et al. (1990) *Plant Breed* 105:33). GSL were extracted from segregating T3 lines and from wild type Columbia controls for HPLC analysis. In 23 T3 lines containing the BoGSL-ALK+ allele, the glucosinolate profile in their leaves was altered by the presence of three additional peaks which were absent in the 9 T3 lines lacking BoGSL-ALK. The profiles of the latter were the same as that observed for the wild type, untransformed ecotype. The three new peaks in the transformed plants carrying BoGSL-ALK+ correspond to 2-hydroxy-3-butenyl (progoitrin), 2-propenyl glucosinolate (sinigrin) and 3-butenyl glucosinolate (gluconapin) (FIG. 7). Therefore, these profiles are consistent with the conclusion that BoGSL-ALK converted in planta more than 80% of 4-methylsulfinylbutyl (glucoraphanin) GSL precursor into 3-butenyl glucosinolate, and the 3-methylsulfinylpropyl (glucoiberin) GSL precursor into 2-propenyl glucosinolate (FIG. 7). The GSL profiles of seeds from the transformed plants displayed a fourth new peak probably corresponding to 2-benzoyloxy-3-butenyl as reported by Kleibenstein et al (*Plant Physiol*. (2001) 126:811). Additionally the content of 4-methylsulfinylbutyl increased, whereas the content of 4-methylthiobutyl, 3-benzoyloxypropyl, and 4-benzoyloxyl-3-butenyl glucosinolates dramatically decreased. This is shown in relative amounts in the histogram depicted in FIG. 8.

For marker assisted selection of a BoGSL-ALK+ allele in segregating populations of *Brassica oleracea*, we have also developed primers FC7-FC8 [FC7 5'ATGTGTTGATTCT-GCCGAG 3' (SEQ ID NO:21); FC8, 5' GTGCTTTACT-GTTTGCTCC 3' (SEQ ID NO:22)]. Additionally, primers ODD14-ODD15 [ODD14 5' TCG-GTCTTTGTCGTTTTCTA 3' (SEQ ID NO:29); ODD15 5' GCGAGGATGCTACTGGTT 3' (SEQ ID NO:30)] can be used to amplify a co-dominant microsatellite marker located in the same BAC clone as the BoGSL-ALK at a distance where genetic recombination is very unlikely. The genomic and coding sequences disclosed in this application can be used to construct additional primers as needed.

Example 4

Localization and Tagging of the BoGSL-Elong Gene

In this example the gene encoding BoGSL-ELONG is identified and sequenced.

Materials and Methods

Plant Materials.

Twenty six commercial varieties of three different *Brassica oleracea* crops, broccoli, cauliflower and collard, and four doubled haploid lines of broccoli and cauliflower were included in the present study (Table 4).

TABLE 4

List of B. oleracea cultivars used in the present study

| ID | Name | Type | Crop |
|---|---|---|---|
| B122 | April | Open pollinated | white cauliflower |
| B130 | Snow King | Open pollinated | white cauliflower |
| B207 | White Christmas | Open pollinated | white cauliflower |
| B208 | 343 Self Blanching | Open pollinated | white cauliflower |
| B264 | Snowball 76 | Open pollinated | white cauliflower |
| B267 | White Top | Open pollinated | white cauliflower |
| B272 | Snow March | Open pollinated | white cauliflower |
| B312 | Canberra | Open pollinated | white cauliflower |
| B1808 | Snow Crown | Open pollinated | white cauliflower |
| B1812 | White Magic | Open pollinated | white cauliflower |
| B1804 | Guardian | F1 hybrid | white cauliflower |
| B1821 | Fargo - F1 Hybrid | F1 hybrid | white cauliflower |
| A1 | Bai-Jiu | F1 hybrid and DH lines | white cauliflower |
| A2 | An-Nan Early | F1 hybrid and DH lines | white cauliflower |
| B314 | Cavolifiore di Sicili | Open pollinated | purple cauliflower |
| B485 | Violet Queen | Open pollinated | purple cauliflower |
| B265 | Cauliflower Purple | Open pollinated | purple cauliflower |
| B10-10 | Early Big | DH lines | broccoli |
| B12 | Li-Lu | F1 hybrid and DH lines | broccoli |
| B15 | Lu-Ling | F1 hybrid and DH lines | broccoli |
| B93 | Topper43-70 | Open pollinated | broccoli |
| B104 | Georgia | Open pollinated | collard |

DNA Amplification and Library Screening

Using the sequence of the GS-ELONG candidate genes from *Arabidopsis*, (IPMS-At1, IPMS-At2), a pair of primers was designed, IPMI, 5'-GCCATCTTCGCACCCAAA-3' (SEQ ID NO:31) and IPM2, 5'-GTGACGGTGAA-CAATCTCCT-3' (SEQ ID NO:23), to amplify the corresponding region of the *Brassica oleracea* homolog. These primers were designed to amplify part of exon 1, exon 2 and the intervening intron between these two exons. For this purpose we used broccoli genomic DNA. The PCR conditions for amplification were: 94° C., 1 min., 56° C., 1 min., 72° C., 2 min., for 35 cycles. The resulting amplified DNA was confirmed to correspond to the IPMS genes by sequencing.

Primers IPM1 and IPM2 were then used to screen a BAC library constructed with the broccoli doubled haploid line 'Early Big-10' (Quiros et al. (2001) *Genetics* 157:1321) for clones harboring IPMS *Brassica* homologs. Two rounds of PCR were used for the library screening by 3-D pooling of the clones following the strategy of Koes et al. (*Proc Natl Acad Sci USA* (1995) 92:8149).

Partial BAC sequencing was done using the SRAP protocol as described by Li and Quiros (*Theor Appl Genet* (2001) 103:455). Plasmid DNA from BAC clones was prepared following the plasmid mini preparation protocol as described by Sambrook et al. (1989, supra). DNA was fingerprinted using the SRAP protocol. Procedures for DNA collection from the gels and sequencing were as those reported by Li and Quiros (2001, supra).

Co-Segregation Analysis: A F2 population of 450 plants, generated by crossing doubled haploid lines from cauliflower (An-Nan-83) and broccoli (Early Big-10), was used for co-segregation analysis between 4C GSL and the IPMS candidate genes. This population was previously used for genetic analysis of the aliphatic GSL biosynthesis (Li et al., 2001, supra). A third primer (IMP9), based on the *Brassica* IPMS homolog together with primer IPM2 were used to amplify DNA from individual plants of the F2 population. The sequence of IPM9 was: 5'-GTAGTATTCT-CAAAATCTTGT-3' (SEQ ID NO:24). The PCR conditions were the same as those described above. The amplified products were separated using a LI-COR IR2 sequencer (LI-COR Inc. Lincoln, Neb. USA).

Gene Expression Analysis.

We used RT-PCR to do gene expression analysis. We designed primers located in exon 3, 5'-AAGCGAT-CAAAGCGGGTG-3' (SEQ ID NO:32), and exon 4, 5'-CT-TCAAGCGGTGCATTCC-3' (SEQ ID NO:33), where a splicing site change in the candidate *B. oleracea* gene IMPS BoGLS-ELONG occurs in white cauliflowers. For RT-PCR, total RNA was prepared as described by Sambrook et al. (1989, supra). 10 µg RNA was used to do reverse transcription using the RT-PCR kit from Life Technologies (California, USA).

Glucosinolate Determination

Glucosinolate profiles in leaves were determined by HPLC using the method described by Kraling et al. (1990, supra) with some modifications. We corrected the data for UV response factors for different types of glucosinolates (Wathelet et al., GCIRC Technical Meeting, Poznan, Poland, Jun. 5-7, 2001).

Results

Amplification of broccoli DNA with the IPMS primers produced one band displaying sequence identities of 86.3% and 85.0% with exons 1 and 2 of IPMS-At1 and IPMS-At2, respectively.

In total we isolated 16 BAC clones from the broccoli library with the IPMS designed primers. These BAC clones were divided into three putative cistronic groups according to their sequence similarity to IPMS-At genes and to their BAC-end sequences. One of these three groups consisted of five BAC clones, B5B10, B11I7, B13D10, B19N3, and B39I16. addition to the conserved portion of IPMs-At genes, all five clones had one end sequence that matched with that next to the IPMs-At gene in *Arabidopsis*. Furthermore, the end sequences of B5B10, B19N3 and B39I16 were similar to that of *Arabidopsis* gene MYJ24.14, and those of B11I7 and B13D10, to gene MKD15.5. BAC clone MKD15 containing this gene is contiguous to clone MYJ24. In total, 15 fragments of broccoli BAC B19N3 were sequenced using the SRAP protocol. After BLAST analysis, we found one fragment that matched *Arabidosis* gene, MYJ24.2, which is next to IPMS-At2, (MYJ24.1). These results indicated that these five BAC clones contained the IPMS-At homolog (IPMS-Bo), likely matching the IPMS genes in *Arabidopsis*. Through direct BAC sequencing, we obtained the complete sequence of the IPMS-Bo (GenBank accession# AF399834). Similar to IPMS-At1 and IPMS-At2, IPMS-Bo also contains 10 exons. Except for exon 1 and exon 10, all others share the same size in all three genes. At the amino acid level, IPMS-Bo shares 78% and 75% identity to IPMS-At1 and IPMS-At2, respectively. The size of intron 1 of IPMS-Bo is considerably larger, being twice the size of the corresponding intron in IPMS-At1, and four times that of IPMS-At2. Based on this analysis, IPMS-Bo has higher similarity to IPMS-At1 than to IPMS-At2 (Table 5).

TABLE 5

Exon and intron sizes (bp) of two IPMS-At genes of *Arabidopsis*
and homologous alleles (IPMS-Bo) from broccoli and cauliflower.

| Homolog | Exon 1 | Exon 2 | Exon 3 | Exon 4 | Exon 5 | Exon 6 | Exon 7 | Exon 8 | Exon 9 | Exon 10 |
|---|---|---|---|---|---|---|---|---|---|---|
| IPMS-Bo (broccoli) | 378 | 260 | 214 | 81 | 93 | 87 | 101 | 34 | 75 | 141 |
| IPMS-Bo (cauliflow) | 378 | 260 | 404 (214 + 109 + 81)† | | 93 | 87 | 101 | 34 | 75 | 141 |
| IPMS-At1 | 444 | 260 | 214 | 81 | 93 | 87 | 101 | 34 | 75 | 132 |
| IPMS-At2 | 444 | 260 | 214 | 81 | 93 | 87 | 101 | 34 | 75 | 123 |

| Homolog | Intron 1 | Intron 2 | Intron 3 | Intron 4 | Intron 5 | Intron 6 | Intron 7 | Intron 8 | Intron 9 | Total size |
|---|---|---|---|---|---|---|---|---|---|---|
| IPMS-Bo (broccoli) | 1384 | 469 | 99 | 187 | 83 | 94 | 118 | 125 | 179 | 4202 |
| IPMS-Bo (cauliflow) | 1354 | 469 | 0 | 187 | 83 | 94 | 118 | 125 | 179 | 4182 |
| IPMS-At1 | 677 | 501 | 130 | 90 | 86 | 204 | 92 | 102 | 194 | 3597 |
| IPMS-At2 | 299 | 397 | 110 | 495 | 107 | 92 | 105 | 166 | 149 | 3932 |

†fusion of exon 3, intron 3 and exon 4.

In order to confirm that candidate gene IPMS-Bo corresponded to the BoGSL-ELONG, we amplified DNA from the parental lines of the segregating F2 population resulting from crossing cauliflower and broccoli using primers IPM9 and IPM2. Using these primers, we successfully developed a codominant marker, which detected a 30 bp deletion in intron 1 in cauliflower. Among 383 plants of the F2 population, there were 89 plants lacking 4C GSL and all these plants were homozygous for the smaller size cauliflower marker. Therefore, there was complete co-segregation between 4C GSL content and the IPMS-based marker.

Initially, our genetic analysis was mainly focused on the parental lines and their derived segregating population. In this preliminary survey we had observed that white cauliflower varieties did not have 4C GSL. To confirm this observation, we extended our GSL survey to the varieties and doubled haploid lines listed in Table 4. Among the varieties, there were 15 white cauliflowers, three purple cauliflowers, four broccolis, and a collard (Table 4). The glucosinolate composition of this material is presented in Table 6. All white cauliflower varieties had phenotype BoGLS-ELONG–/BoGSL-PRO+/BoGSL-ALK+ since they contained exclusively 3C GSL (glucoiberin and sinigrin or only glucoiberin). All three purple cauliflower varieties contained either the 4C GSL (glucoraphanin) or both 4C and 3C GSL (glucoiberin and glucoraphanin). Accession B314 and B485 containing 3C and 4C GSL had phenotype BoGSL-ELONG+/GSL-PRO-+/GSL-ALK– whereas B265 had phenotype BoGSL-ELONG+/BoGSL-PRO–/BoGSL-ALK–. On the other hand, the broccoli varieties had exclusively 4C GSL, glucoraphanin, that is, phenotype BoGSL-ELONG+/GSL-PRO-+/GSL-ALK– whereas in the collard variety, sinigrin (3C) and progoitrin (4C) were the predominant GSL (over 90% of total aliphatic GSL). Therefore the phenotype of this crop was BoGSL-ELONG+/BoGSL-PRO–/BoGSL-ALK+.

TABLE 6

Glucosinolate content for the *Brassica* varieties and doubled haploid lines used in the present study.

| ID | 1 | 2 | 3 | 4 | 5 | 6 | 7 | 8 | Total |
|---|---|---|---|---|---|---|---|---|---|
| Varieties | | | | | | | | | |
| B122 | 0.064 | 0 | 0 | 0.176 | 0.056 | 1.081 | 0.059 | 0.121 | 1.553 |
| B130 | 0.055 | 0 | 0 | 0.091 | 0.028 | 0.969 | 0.068 | 0.229 | 1.438 |
| B207 | 0.14 | 0 | 0 | 0.108 | 0.048 | 0.722 | 0.073 | 0.104 | 1.193 |
| B208 | 0.061 | 0 | 0 | 0.092 | 0.023 | 0.844 | 0.072 | 0.103 | 1.193 |
| B264 | 0.061 | 0 | 0 | 0.174 | 0.031 | 1.158 | 0.064 | 0.097 | 1.582 |
| B267 | 0.08 | 0 | 0 | 0.077 | 0.013 | 0.602 | 0.035 | 0.114 | 0.919 |
| B272 | 0.089 | 0 | 0 | 0.094 | 0.019 | 0.444 | 0.046 | 0.049 | 0.737 |
| B312 | 0.076 | 0 | 0 | 0.119 | 0.069 | 0.711 | 0.094 | 0.069 | 1.135 |
| B1808 | 0.093 | 0 | 0 | 0.264 | 0.044 | 0.85 | 0.052 | 0.15 | 1.45 |
| B1812 | 0.087 | 0 | 0 | 0.09 | 0.022 | 0.454 | 0.042 | 0.079 | 0.771 |
| B1804 | 0.078 | 0 | 0 | 0.124 | 0.05 | 0.617 | 0.044 | 0.119 | 1.029 |
| B1821 | 0.089 | 0 | 0 | 0.05 | 0.024 | 0.58 | 0.046 | 0.064 | 0.851 |
| B314 | 0.057 | 0 | 0.029 | 0 | 0.064 | 1.602 | 0.099 | 0.044 | 1.891 |
| B485 | 0.049 | 0 | 0.154 | 0 | 0.038 | 1.101 | 0.098 | 0.029 | 1.466 |
| B265 | 0 | 0 | 0.06 | 0 | 0.026 | 1.123 | 0.089 | 0.01 | 1.306 |
| B10-10 | 0 | 0 | 0.095 | 0 | 0.034 | 0.679 | 0.08 | 0.098 | 0.984 |
| B93 | 0 | 0 | 0.055 | 0 | 0.001 | 0.458 | 0.039 | 0.013 | 0.565 |
| B104 | 0.047 | 0.674 | 0.056 | 1.104 | 0.044 | 0.008 | 0.013 | 0 | 2.033 |
| DH lines | | | | | | | | | |
| A1F1 | 0.266 | 0 | 0 | 0.04 | 0 | 0.252 | 0.025 | 0 | 0.58 |
| A1-75 | 0.162 | 0 | 0 | 0 | 0 | 0.086 | 0.015 | 0 | 0.262 |
| A1-94 | 0.071 | 0 | 0 | 0.029 | 0 | 0.09 | 0.022 | 0 | 0.211 |
| A1-104 | 0.119 | 0 | 0 | 0.019 | 0 | 0.211 | 0.02 | 0 | 0.368 |
| A1-143 | 0.169 | 0 | 0 | 0.028 | 0 | 0.283 | 0.021 | 0.018 | 0.518 |
| A1-262 | 0.112 | 0 | 0 | 0.052 | 0 | 0.317 | 0.035 | 0 | 0.515 |
| A1-402 | 0.113 | 0 | 0 | 0 | 0 | 0.298 | 0.016 | 0 | 0.426 |
| A1-393 | 0.036 | 0 | 0 | 0.025 | 0 | 0.116 | 0.021 | 0 | 0.196 |
| A1-409 | 0.121 | 0 | 0 | 0 | 0 | 0.327 | 0.044 | 0.01 | 0.501 |
| A1-431 | 0.048 | 0 | 0 | 0.024 | 0 | 0.155 | 0.017 | 0.008 | 0.25 |
| A1-464 | 0.214 | 0 | 0 | 0.065 | 0 | 0.481 | 0.033 | 0.019 | 0.811 |
| A155F1 | 0.556 | 0 | 0 | 0.047 | 0.005 | 0.466 | 0.054 | 0.005 | 1.131 |
| A155-7 | 0.317 | 0 | 0 | 0.08 | 0.009 | 0.362 | 0.053 | 0 | 0.819 |
| A155-13 | 0.048 | 0 | 0 | 0.043 | 0 | 0.5 | 0.046 | 0 | 0.636 |
| A155-18 | 0.364 | 0 | 0 | 0.134 | 0 | 0.26 | 0.059 | 0.012 | 0.827 |
| A155-30 | 1.065 | 0 | 0 | 0.166 | 0.016 | 0.6 | 0.063 | 0.063 | 1.97 |
| A155-38 | 0.962 | 0 | 0 | 0 | 0 | 0.218 | 0.043 | 0.012 | 1.234 |

TABLE 6-continued

Glucosinolate content for the *Brassica* varieties and doubled haploid lines used in the present study.

| ID | 1 | 2 | 3 | 4 | 5 | 6 | 7 | 8 | Total |
|---|---|---|---|---|---|---|---|---|---|
| A155-43 | 0.578 | 0 | 0 | 0 | 0.008 | 0.414 | 0.068 | 0.026 | 1.092 |
| A155-49 | 0.236 | 0 | 0 | 0 | 0.007 | 0.558 | 0.015 | 0 | 0.814 |
| A155-56 | 0.594 | 0 | 0 | 0 | 0.007 | 0.576 | 0.073 | 0.07 | 1.318 |
| A155-78 | 0.203 | 0 | 0 | 0.078 | 0.008 | 0.561 | 0.078 | 0 | 0.926 |
| B12F1 | 0 | 0 | 0.107 | 0 | 0 | 0.226 | 0.029 | 0.02 | 0.38 |
| B12-3 | 0 | 0 | 0.065 | 0 | 0 | 0.17 | 0.014 | 0.052 | 0.3 |
| B12-6 | 0 | 0 | 0.086 | 0 | 0 | 0.217 | 0.04 | 0.031 | 0.373 |
| B12-9 | 0 | 0 | 0.084 | 0 | 0 | 0.218 | 0.027 | 0.15 | 0.478 |
| B12-10 | 0 | 0 | 0.058 | 0 | 0 | 0.194 | 0.034 | 0.049 | 0.334 |
| B12-15 | 0 | 0 | 0.061 | 0 | 0 | 0.48 | 0.035 | 0.031 | 0.605 |
| B12-22 | 0 | 0 | 0.099 | 0 | 0 | 0.283 | 0.029 | 0.089 | 0.499 |
| B12-36 | 0 | 0 | 0.057 | 0 | 0 | 0.147 | 0.033 | 0.14 | 0.376 |
| B12-34 | 0 | 0 | 0.111 | 0 | 0 | 0.107 | 0.027 | 0.093 | 0.337 |
| B15F1 | 0 | 0 | 0.063 | 0 | 0 | 0.105 | 0.02 | 0.01 | 0.197 |
| B15-121 | 0 | 0 | 0.02 | 0 | 0 | 0.075 | 0.016 | 0.026 | 0.137 |
| B15-156 | 0 | 0 | 0.053 | 0 | 0 | 0.264 | 0.026 | 0 | 0.342 |
| B15-200 | 0 | 0 | 0.041 | 0 | 0 | 0.109 | 0.012 | 0.026 | 0.186 |
| B15-223 | 0 | 0 | 0.042 | 0 | 0 | 0.097 | 0.027 | 0.006 | 0.17 |
| B15-254 | 0 | 0 | 0.079 | 0 | 0 | 0.198 | 0.028 | 0.033 | 0.336 |
| B15-272 | 0 | 0 | 0.041 | 0 | 0 | 0.127 | 0.041 | 0.018 | 0.225 |
| B15-411 | 0 | 0 | 0.104 | 0 | 0 | 0.108 | 0.03 | 0.021 | 0.26 |
| B15-436 | 0 | 0 | 0.147 | 0 | 0 | 0.127 | 0.018 | 0.019 | 0.31 |
| B15-501 | 0 | 0 | 0.046 | 0 | 0 | 0.109 | 0.019 | 0.013 | 0.185 |

1. 3-Methylsulfinylpropyl (glucoiberin, 3C),
2. 2-hydroxy-3-butenyl (progoitrin, 4C),
3. 4-Methylsulfinylbutyl (glucorapganin, 4C),
4. 2-propenyl (sinigrin, 3C),
5. hydroxy-indolyl-3-methyl (4-hydroxy-glucobrassicin),
6. indolyl-3-methyl (glucobrassicin),
7. 4-methoxy-indolyl-3-methyl (4-methoxy-glucobrassicin),
8. 1-methoxy-indolyl-3-methyl (neoglucobrassicin).

GSL analysis was also performed in two white cauliflower doubled haploid line populations, in two broccoli doubled haploid line populations, and in their original F1 hybrid parental varieties. The same results were obtained as those described above, where white cauliflower had only 3C glucosinolates and broccoli 4C glucosinolates. Noteworthy is the fact that sinigrin segregated among the cauliflower doubled haploid lines, indicating that the desaturation gene BoGSL-ALK was heterozygous in both F1 hybrid parental varieties of these lines. The broccoli DH lines had only glucoraphanin, indicating BoGSL-ALK was null in this material.

Having obtained the sequence of candidate gene BoGSL-ELONG (FIG. 9), we proceeded to determine whether this gene was expressed in the *B. oleracea* varieties. All white cauliflower varieties tested were considered phenotypically as BoGSL-ELONG– since they lacked 4C GSL, and therefore were expected to carry the null allele for this gene. On the other hand the broccoli varieties tested had 4C GSL thus being BoGSL-ELONG+. When we performed RT-PCR with cDNA from broccoli and white cauliflower with the primers based on the sequence of BoGSL-ELONG, we detected a polymorphism resulting in bands of two different sizes for each crop type. After sequencing both bands, we found that a mutation in the white cauliflower allele caused a splicing site change (intron 3 fails to excise) resulting in a larger size cDNA (Table 5). The larger size cDNA band co-segregated with the absence of 4C GSL in the F2 population of broccoli×cauliflower. This allele was present in all white cauliflower varieties and DH lines we tested.

Example 5

Localization and Tagging of the BoGSL-PRO Gene

For the gene controlling synthesis of 3-C side chain glucosinolates, several SRAP markers have been found. Sequencing these markers enabled the identification of *B. oleracea* BAC clones anchoring these markers. Through partial sequencing of the *B. oleracea* BAC clones, sequences that matched with one *Arabidopsis* BAC clone located on chromosome 4 were identified. From these sequences we developed two sets of primers: Ce6-Ce7, which amplify a dominant marker associated with BoGSL-PRO⁻allele [Ce6, 5'CGAATTTTAGGGTATCCATA 3' (SEQ ID NO:25); Ce7, 5'GTACTGCATGGAGTGAGAA 3' (SEQ ID NO:26)] and Ce39-Ce40, [Ce39, 5'GAATGTCCTAAAATCAATACT 3' (SEQ ID NO:27); Ce40, 5'TTTTCACTAGCGTTCCAATT 3' (SEQ ID NO:28)] which amplify co-dominant microsatellite (SSR) markers for both alleles of the BoGSL-PRO gene. These markers can be used by breeders for marker assisted selection of specific alleles in their segregating populations to obtain genotypes for a specific glucosinolate composition.

The above examples demonstrate how sequence-related amplified polymorphism (SRAP) can be used to efficiently identify and amplify open reading frames from any plant genomic sequence. The application of SRAP was used to localize and identify the sequences of several *Brassica oleracea* genes encoding enzymes involved in the synthesis of glucosinolate molecules, including BoGSL-ALK, BoGSL-ELONG and BoGSL-PRO. The successful modification of glucosinolate profile in an *Arabidopsis* plant transformed with a BoGSL-ALK gene demonstrates how genes in the glucosinolate pathway can be effectively used to rationally alter the glucosinolate content of a plant as desired.

Example 6

Marker Assisted Selection for Specific Glucosinolate Content of *B. oleracea* Crops Destined for Human Consumption or as Biofumigants The following existing breeding populations are employed to accomplish this objective:
1) Two recombinant inbreeds (RI) advanced to F4 and F5 generations resulting from crossing collard×broccoli and collard×purple cauliflower.
2) An F3 population from broccoli×cauliflower doubled haploids.
3) An F2 population resulting from crossing doubled haploid broccoli×*B. macrocarpa*.

Seeds from recombinant inbred lines are planted for horticultural evaluation to determine whether they approach broccoli and cauliflower type, and are screened for self-fertility and uniformity of glucoraphanin content.

From the F3 broccoli×cauliflower population, consisting of approximately 150 lines, using the markers for the three major GSL genes plants of two different genotypes are selected. Plants with the first, BoGSL-PRO+/BoGSL-ELONG−/BoGSL-ALK+, will produce primarily sinigrin, and find use as green manure crops for soil biofumigation. The second genotype targeted for selection is BoGSL-PRO−/BoGSL-ELONG+BoGSL-ALK−. Plants of this genotype will accumulate glucoraphanin, and broccoli and cauliflower types with high self-fertility are selected from these plants. For the high sinigrin lines destined to green manure use, the seed are increased for release. For this purpose, the selected plants are intercrossed to produce open pollinated (OP) seed. Individual selection for self-fertility is performed to isolate parental lines for the generation of high sinigrin OP varieties in the future. For the high sulfurophane broccoli and cauliflower lines an additional cycle of backcrossing to their respective doubled haploid parents is performed to improve type. Again selection for GSL genotype and uniformity, and horticultural type is performed. OP lines are generated for future release as high sulfurophane broccoli and cauliflower varieties.

From the third population, which is the farthest removed from commercial types due to the use of the *B. macrocarpa* parent, the desired GSL genotype is again selected using the three marker sets. This population consists of approximately 150 plants, but more could be generated if necessary. Plants with high sinigrin and high glucoraphanin are selected and tested for self-fertility. The wild parent has the potential to produce a higher content of sinigrin than any variety of any *Brassica* crop. Therefore, it is possible to generate OP lines with particularly high sinigrin content from this material for use as green manure crops. High biomass content rather than horticultural traits is selected for these crops. Recombinants producing very high glucoraphanin content are also selected from the segregating progenies for possible use a sprouts.

Once the plants with the desired GSL genotype have been selected, their GSL type and content is confirmed by HPLC using the procedure of Kraling (1990, supra).

For the marker selection, a LI-COR sequencer (LI-COR Inc. Lincoln, Neb. USA) is used, which allows the visualization of the marker bands we have developed for all three GSL genes.

Plant DNA is extracted by a simplified CTAB procedure (Saghai-Maroof et al. (1984) *Proc. Natl. Acad. Sci.* 81:8014) in 2× buffer: 100 mM Tris-HCl, 1.4 M NaCl, 20 mM EDTA, 2% CTAB, pH 8.0. SRAP markers are used for tagging BoGSL-ALK, BoGSL-ELONG and BoGSL-PRO as described above. For the selection of alleles for the gene BoGSL-ALKc primers ODD14 5'-TCGGTCTTTGTCGTTTTCTA-3' (SEQ ID NO:29) and ODD15 5'-GCGAGGATGCTACTGGTT-3' (SEQ ID NO:30) are used. These amplify a co-dominant microsatellite marker located in the same BAC clone as the BoGSL-ALK at a distance where genetic recombination is very unlikely (less than 50 Kb). For selection of alleles for the gene BoGSL-ELONG primers IPM1, 5'-GCCATCTTCGCACCCAAA-3' (SEQ ID NO:31) and IPM9, 5'-GTAGTATTCT-CAAAATCTTGT-3' (SEQ ID NO:24) are used to amplify the markers for this gene. The IPM1-IPM9 primers amplify part of exon 1, exon 2 and the intervening intron between these two exons. For selection of alleles for the gene BoGSL-PRO primers Ce39, 5'-GAATGTCCTAAAAT-CAATACT-3' (SEQ ID NO:27) and Ce40, 5'-TTTTCAC-TAGCGTTCCAATT-3' (SEQ ID NO:28) The Ce39-Ce40 primers amplify a microsatellite sequence next to the BoGSL-PRO gene. All primers are labeled by LI-COR fluorochromes. The PCR conditions for amplification are: 94° C., 1 min., 56° C., 1 min., 72° C., 2 min., for 35 cycles. The amplified prod separated using a LI-COR IR2 sequencer.

Example 7

Development of Open Pollinated/Self Fertile Inbred Lines with Specific GSL Content Selected recombinant inbred plants, with high glucoraphanin content based on marker alleles and confirmed by HPLC analysis, are grown to maturity in the greenhouse to determine their horticultural type (broccoli or cauliflower), self seed setting ability (grams of seed per plant in absence of pollinators, compared to seed set by hand pollination of 5 plants of variety 'Brigadier'). Seed from these plants are grown in the field and tested for GSL content, uniformity and horticultural type. Those that approach type and have glucoraphanin levels close to 4 µM/gr fresh weight (FW) are caged for seed increase. Seed germination tests are performed to determine their potential for sprout production. Only those with 90% germination are selected. For the plants selected by broccoli×cauliflower F3 population, segregation for GSL and type are expected. Therefore, at least two additional backcrosses are carried out to produce fixed lines from this material.

For the lines to be used as green manure crops, high sinigrin content and high biomass is selected. Seed from the high sinigrin plants (>10 µM/gr FW) are grown and evaluated for self-fertility in the greenhouse and in the field.

Example 8

Development of Chinese Cabbage with Glucoraphanin

A collection of existing eight *B. rapa-B. oleracea* monosomic addition lines (McGrath, et al 1990, supra) are planted for screening with the BoGSL-ALK primers. Plants from those lines containing the *B. oleracea* chromosome carrying this gene are selected and selfed or intercrossed to promote introgression of this gene into the *B. rapa* chromosomes. Ideally, the broccoli allele replaces the *B. rapa* alleles for this gene. This event occurs at the rate of about 5 in 100 plants in these lines, so a progeny of 500 seeds are generated that are screened for introgression of the BoGSL-ALK allele using the primers ODD14-ODD15. Progenies from the selected plants are screened again with the markers and GSL content is confirmed by HPLC analysis. Meiotic inspection of pollen mother cells (Quiros et al 1987, supra) is performed to confirm introgression and meiotic stability in these lines. Upon detection of diploid *B. rapa* plants with glucoraphanin, new lines are extracted from a Chinese cabbage×broccoli tetraploid hybrid. This is backcrossed 3 times to Chinese cabbage to eliminate the broccoli chromosomes, excepting the one carrying the BoGSL-ALK allele. Once this line is identified, it is selfed to induce introgression and replacement of the *B. rapa* alleles by the non-functional broccoli allele.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. An isolated nucleic acid comprising a DNA sequence which is at least 95% identical to SEQ ID NO:3, wherein said nucleic acid encodes a glucosinolate alkenylation/desaturation enzyme (GSL-ALK).

2. An isolated nucleic acid comprising a DNA sequence which encodes an alkenylation/desaturation enzyme (GSL-ALK) comprising an amino acid sequence which is at least 95% identical to SEO ID NO:4.

3. The nucleic acid according to claim 1, wherein said DNA sequence is SEQ ID NO:3.

4. A DNA construct comprising the nucleic acid according to claim 1.

5. A DNA construct comprising the nucleic acid according to claim 2.

6. A DNA construct comprising a nucleic acid sequence operably linked to a plant promoter wherein the nucleic acid sequence is an antisense of the isolated nucleic acid of claim 1.

7. A transformed seed comprising a recombinant expression cassette comprising a plant promoter operably linked to a nucleic acid sequence encoding a glucosinolate alkenylation/desaturation enzyme (GSL-ALK) comprising an amino acid sequence which is at least 95% identical to SEQ ID NO: 4.

8. A transformed plant comprising a recombinant expression cassette comprising a plant promoter operably linked to a nucleic acid sequence encoding a glucosinolate alkenylation/desaturation enzyme (GSL-ALK) comprising an amino acid sequence which is at least 95% identical to SEQ ID NO: 4.

9. A method of modifying the glucosinolate profile in a Brassica plant, said method comprising the step of: a) introducing into a Brassica plant a construct comprising a nucleic acid sequence which encodes glucosinolate alkenylation/desaturation enzyme (GSL-ALK) comprising an amino acid sequence which is at least 95% identical to SEQ ID NO: 4, wherein the nucleic acid sequence is operably linked to a plant promoter in the sense orientation in said construct; and b) expressing the GSL-ALK enzyme, whereby said glucosinolate profile is modified as compared to a non transgenic Brassica plant.

10. The method of claim 9, wherein said construct is introduced into a plant using Agrobacterium.

11. The method of claim 9, wherein the nucleic acid sequence is SEQ ID NO: 3.

12. The method of claim 9, wherein modifying the glucosinolate profile is decreasing the amount of a glucosinolate selected from the group consisting of glucoraphanin and glucoiberin.

13. The method of claim 9, wherein modifying the glucosinolate profile is increasing the amount of glucosinolate selected from the group consisting of gluconapin and sinigrin.

14. A method of modifying the glucosinolate profile in a Brassica plant, said method comprising the step of: a) introducing into a Brassica plant a construct comprising a glucosinolate alkenylation/desaturation enzyme (GSL-ALK) nucleic acid sequence comprising SEQ ID NO: 3, wherein the GSL-ALK nucleic acid sequence is operably linked to a plant promoter in the antisense orientation in said construct; and b) expressing the GSL-ALK nucleic acid sequence, whereby said glucosinolate profile is modified as compared to a non transgenic Brassica plant.

15. The method of claim 14, wherein said construct is introduced into a plant using Agrobacterium.

16. The method of claim 14, wherein modifying the glucosinolate profile is increasing the amount of a glucosinolate selected from the group consisting of glucoraphanin and glucoiberin.

17. The method of claim 14, wherein modifying the glucosinolate profile is decreasing the amount of a glucosinolate selected from the group consisting of gluconapin and sinigrin.

* * * * *

```
                       SEQUENCE LISTING

<160> NUMBER OF SEQ ID NOS: 41

<210> SEQ ID NO 1
<211> LENGTH: 2939
<212> TYPE: DNA
<213> ORGANISM: Brassica oleracea (italica group)
<220> FEATURE:
<223> OTHER INFORMATION: genomic BoGSL-ALK gene from broccoli

<400> SEQUENCE: 1
aaaaaaaaaa aatagaatgt ttctgtctat aaatgggcat tccatcattt actttctcag      60
tacggaagca aaaaaaaaac taaggaaaag aaaaccagct tgatctcttt gaatcaaaga     120
aaaactccaa aggtagttgt cttatgagtt tttaatgttt tcttttgttg tgatgattaa     180
agagctactt aaacattttc tttcgggtta aaatataaag ctaattaaca ttttataaat     240
atatttttgg atttgcacca aaggaaaaaa agaatgggtg cagacactcc tcaacttcca     300
gtcatctatc tctcggacca aaccctaaaa ccaggaggtg agaagtgggt tgaagtgagg     360
agtgatgtcc gtaaagctct tgaagactac ggcgcttttg aggtgtcata tgatagagtg     420
tcagaagagc ttaagaagtc agttttggat gccatgatag agcttttcga gttaccagtt     480
gaggctaaac agagaaacgt gtctccgaaa ccttacactg gatattcaac tcataatggt     540
ctctctgaga gtctagggat ccaggattcc aatgttttgg agaaagttaa cgaatttact     600
caactgctac gccctgattg tgagggtaac aagactatga ggtaacgtca tgtcaaaaaa     660
aaaaaaactc agtaatgctt catagagtaa attaattgtt cgtaaattcc tgttaatctt     720
tcatcaaaaa tattttcgta acttttttgct agttgttttt cataagttat gtgacaaatt     780
tctataaaaa accttgtttt tatctttatt tttttggaaa aatgttagtt cactcatata     840
gtaatgaact gaaattttgt tttcaatctc acgtttcacg cattttttt tgtttctatt      900 aaaatagcta tataaattt ctttgtgttg aaaacagcga aacgatccag aagtttttcag     960 agaagttagc agaattggat gtaatggtga aagaatggt catagagagc tttgggatag    1020
aaaactactt tgatgaacac ctcaagtcaa cgaattaccg tttgcgactg atgaagtatg    1080
tagcaccacc tgatgttgat gctaatgttg cggtcagtac taaagattct gttgatggtg    1140
ctaatacgaa tacaactgct aacgctgatg ctggtgatat tgctaatggt attgctaaag    1200
ttcatattga tgacgatgct aatgccaagg gtgacgtttg cactggtgtt ggtaccaatc    1260
ataatggtga tgacgttaat actggtgatt gtgctaatgt taagtctaat gtcgacgttg    1320
gtactaatgt tagtgctaaa tctagtgttg gtgctgatgt taacattggc actattgctg    1380
atgttaaggc taatactggt actcgtacta gtgctaatgt tggcgttagt gatagtgtta    1440
aagctaatgg tggcgcagat gatgaggaga agaaattagg tctaccttct catactgata    1500 aacctttga cggtgcttta tcaatatgag attgaaggtt tggaggtgtt aaccaaagat    1560
gaaaagtgga tcaggttaaa accatctcat aactctttcg ttgttatggc tggagattct    1620
ctatatgtaa gttctaactt atttttatttt taaatgggat gcaccataat atcttaattg    1680
cgatcatcat aataatcata acttttttat gatatatatt ataactttat gatatacata    1740
ttcataactt tatgatataa atattacata attcaccttt ttattatttc ttatcacttt    1800
cacaaatgca tgtcgacgtt actaaagtgt ttatacatta acattatgtt ttcttctcat    1860
```

```
catgaatctt gtgttggttt ttttattatt attttttgc aggcacttat gaatggtaga      1920
ctatctcgtc cgtttcatag agtaagagta acggaaagaa agaagacaag gtattcaata     1980
gcattgttct cgactccaaa cggagattac atcatcgaac caccaaaaga gcttgtggac     2040
gagaagcacc cacgtctctt caaatcattc acttacgttg acttgatgag tttctatcac     2100
actgaggctg gtcgtagacc tcgttctact cttcacgctt attgtgccgt ctctggagca     2160
taaatgtgtg cgcttactta cgagagtttc aacaatgttt aagtagtttc atggttcaac     2220
taatatcaag aactgcatgt agtactaaat aagagttttt ggattagttg agtatatgtg     2280
ttttatttcg ggagaagcaa tcaagtctct cttttgtatg aaaaatcaat aaaaatatgt     2340
gtatgagcat gttcaataat gtaatgaatt tggttggatc tgttggttca caagatgtca     2400
agatcgtaaa taggttaatt aaataggtta atttcttctt ctttttttaaa ctaaattaaa    2460 ttcattttttt tttataaaaa aatactagtt taatttcagg agatgggaaa cgagtgtgga    2520
acatataaaa actggtgttt gcgatttcaa acattaaacg ctaaataagt gaatgattta     2580 cttttcatgtt atcgtagcga cagtggtttt gagtcgacat gtagatcccc cttaccttag    2640
gaatttgttt gtttgcaaaa tgccaaaatc gtaaatagta gtaaattagt aatgttattt     2700
aaagtttgac tggtttaatt gcagtaggtg tatgtgctgt ggtccaaaaa ttagtgaaac     2760
gaataattca attgtaaatt agtaatgtta tttaaaatat agacatgcat tgtctcatga     2820
acaaagtgtt tgaaatagcg atttgcaagt gccaactctc ttcttatgaa caacgttaca     2880
aattaggacc ggcttgggca aaacctaacg aaacattacc tttaataaat cacctttgc      2939
```

<210> SEQ ID NO 2
<211> LENGTH: 2869
<212> TYPE: DNA
<213> ORGANISM: Brassica oleracea (viridis group)
<220> FEATURE:
<223> OTHER INFORMATION: genomic BoGSL-ALK gene from collard

<400> SEQUENCE: 2

```
aaaaaaacct aaggaaaaga aaactagctt gatctctttg aatcaaagaa aactccaaag       60
gtaattttgg taaatgttaa aatactccaa aggtagtttt tcttatgaat tttgaatgtt      120
tcttttgttg tgggtgatta aagagttact taaatatttt ctttcgggtt aaaataaagc      180
taattaatta gtttactaaa aaaaaattaa aaaaaaaata aagctaatta acattttatg      240 aatatattt tttggatttg caccaaaggc gaaaagaatg ggtgcagaca ctcctcaact       300
tccagtcatc tatctctcgg accaaaccct aaaaccagga agtgagaagt ggggttgaagt     360 gaggagtgat gtccgtaaag ctcttgaaga ctacggcgct tttgaggtgt catatgatag      420
agtgtcagaa gagcttaaga agtcagtttt ggatgccatg atagagcttt tcgagttacc      480
agttgaggct aaacagagaa acgtgtctcc gaaaccttac actggatatt caactcataa      540
tggtctctct gagagtctag ggatccagga ttccaatgtt ttggagaaag ttaacgaatt      600
tactcaactg ctacgccctg attgtgaggg taacaagact atgaggtaac gtcatgtcga      660
aaaaaaaaac tcagtaatgc ttcatagagt aaattaattg ttcggaaatt cctgtaatct      720
tcatcaaaaa tatttcgtaa cttttttgcta gttgttttca taggtatgt gacaaatttc      780 tataaaaacc ttgttttttat ctttattttt ttggaaaaat gttagttcac tcatatagta    840
atgaactgaa atttttgtttt caatctcacg tttcacgcat tttttttttgt ttctattaaa   900 atagctatat aaattttttct ttgtgttgaa aacagcgaaa cgatccagaa gttttcagag     960
```

-continued

```
aagttagcag aattggatgt aatggtgaga agaatggtca tagagagctt tgggatagaa    1020
aactactttg atgaacacct caagtcaacg aattaccgtt tgcgactgat gaagtatgta    1080
gcaccacctg atgttgatgc taatgttgcg gtcagtacta agattctgt tgatggtgct    1140 aatacgaata caactgctaa cgctgatgct ggtgatattg ctaatggtat tgctaaagtt    1200
catattgatg acgatgctaa tgccaagggt gacgtttgca ctggtgttgg taccaatcat    1260
aatggtgatg acgttaatac tggtgattgt gctaatgtta agtctaatgt cgacgttggt    1320
actaatgtta gtgctaaatc tagtgttggt gctgatgtta acattggcac tattgctgat    1380
gttaaggcta atactggtac tcgtactagt gctaatgttg gcgttagtga tagtgttaaa    1440
gctaatggtg gcgcagatga tgaggagaag aaattaggtc taccttctca tactgataaa    1500
aaccttttga cggtgcttta tcaatatgag attgaaggtt tggaggtgtt aaccaaagat    1560
gaaaagtgga tcaggttaaa gccatctcat aactctttcg ttgttatggc tggagattct    1620
ctatatgtaa gttctaactt atttatttt taaatgggat gcaccataat atcttaattg    1680
cgatcatcat aataatcata acttttttat gatatatatt ataactttat gatatacata    1740
ttcataactt tatgatataa atattacata attcaccttt ttattatttc ttatcacttt    1800
cacaaatgca tgtcgacgtt actaaagtgt ttatacatta acattatgtt ttcttctcat    1860
catgaatctt gtgttggttt ttttattatt attttttgc aggcacttat gaatggtaga    1920
ctatctcgtc cgtttcatag agtaagagta acggaaagaa agaagacaag gtattcaata    1980
gcattgttct cgactccaaa cggagattac atcatcgaac caccaaaaga gcttgtggac    2040
gagaagcacc cacgtctctt caaaccattc acttacgttg acttgatgag tttctatcac    2100
actgaggctg gtcgtagacc tcgttctact cttcacgctt attgtgccgt ctctggagca    2160
taaatgtgtg cgcttactta cgagagtttc aacaatgttt aagtagtttc atggttcaac    2220
taatatcaag aacttcatgt agtactaaaa taagagtttt tggattagtt gagtatatgt    2280
gttttatttc cggagaagca atcaagtctc tcttttgtat gaaaaatcaa taatgtgtat    2340
gtgtatgagc atgttcaata atgtaatgaa tttggttgga tctgttggtt cacaagatgt    2400
caagatcgta aataggttaa ttaaataggt taatttcttc ttcttttta aactaaatta    2460 aattcatttt tttttctaaa aaatactag tttaatttca ggagatggga aacgagtgtg    2520
gaacatataa aaacgggtgt tgccatttc aaacattaaa cgctaaataa gtgaatgatt    2580
tactttcatg ttatcgtagc gatagtggtc ttgagtcgac atgtagatcc cccttacctt    2640
aggaatttgt ttgtttgcaa aatgccaaaa tcgtaaatag taaattaata atgttatta    2700 aagtttgacc ggtttacttg caataggtgt atgtgctgtg gtccaaaaat tagtgaaact    2760
aataattaca attgtaaatt agtaatgtta tttaaaatat agacatgcat tgtctcatga    2820
acaaagtgtt tgaaatagcg atttgcaagt gccaacactc ttctcatga                2869
```

<210> SEQ ID NO 3
<211> LENGTH: 1320
<212> TYPE: DNA
<213> ORGANISM: Brassica oleracea (viridis group)
<220> FEATURE:
<223> OTHER INFORMATION: BoGSL-ALK coding sequence from collard

<400> SEQUENCE: 3

```
atgggtgcag acactcctca acttccagtc atctatctct cggaccaaac cctaaaacca      60
ggaagtgaga agtgggttga agtgaggagt gatgtccgta aagctcttga agactacggc     120
gcttttgagg tgtcatatga tagagtgtca gaagagctta agaagtcagt tttggatgcc     180
```

```
atgatagagc ttttcgagtt accagttgag gctaaacaga gaaacgtgtc tccgaaacct    240
tacactggat attcaactca taatggtctc tctgagagtc tagggatcca ggattccaat    300
gttttggaga agttaacga atttactcaa ctgctacgcc ctgattgtga gggtaacaag    360
actatgagcg aaacgatcca gaagttttca gagaagttag cagaattgga tgtaatggtg    420
agaagaatgg tcatagagag ctttgggata gaaaactact ttgatgaaca cctcaagtca    480
acgaattacc gtttgcgact gatgaagtat gtagcaccac ctgatgttga tgctaatgtt    540
gcggtcagta ctaaagattc tgttgatggt gctaatacga atacaactgc taacgctgat    600
gctggtgata ttgctaatgg tattgctaaa gttcatattg atgacgatgc taatgccaag    660
ggtgacgttt gcactggtgt tggtaccaat cataatggtg atgacgttaa tactggtgat    720
tgtgctaatg ttaagtctaa tgtcgacgtt ggtactaatg ttagtgctaa atctagtgtt    780
ggtgctgatg ttaacattgg cactattgct gatgttaagg ctaatactgg tactcgtact    840
agtgctaatg ttggcgttag tgatagtgtt aaagctaatg gtggcgcaga tgatgaggag    900
aagaaattag gtctaccttc tcatactgat aaaaaccttt tgacggtgct ttatcaatat    960
gagattgaag gtttggaggt gttaaccaaa gatgaaaagt ggatcaggtt aaagccatct   1020
cataactctt tcgttgttat ggctggagat tctctatatg cacttatgaa tggtagacta   1080
tctcgtccgt ttcatagagt aagagtaacg gaaagaaaga agacaaggta ttcaatagca   1140
ttgttctcga ctccaaacgg agattacatc atcgaaccac caaaagagct tgtggacgag   1200
aagcacccac gtctcttcaa accattcact tacgttgact tgatgagttt ctatcacact   1260
gaggctggtc gtagacctcg ttctactctt cacgcttatt gtgccgtctc tggagcataa   1320
```

<210> SEQ ID NO 4
<211> LENGTH: 439
<212> TYPE: PRT
<213> ORGANISM: Brassica oleracea (viridis group)
<220> FEATURE:
<223> OTHER INFORMATION: BoGSL-ALK from collard

<400> SEQUENCE: 4

```
Met Gly Ala Asp Thr Pro Gln Leu Pro Val Ile Tyr Leu Ser Asp Gln
1               5                   10                  15

Thr Leu Lys Pro Gly Ser Glu Lys Trp Val Glu Val Arg Ser Asp Val
            20                  25                  30

Arg Lys Ala Leu Glu Asp Tyr Gly Ala Phe Glu Val Ser Tyr Asp Arg
        35                  40                  45

Val Ser Glu Glu Leu Lys Lys Ser Val Leu Asp Ala Met Ile Glu Leu
    50                  55                  60

Phe Glu Leu Pro Val Glu Ala Lys Gln Arg Asn Val Ser Pro Lys Pro
65                  70                  75                  80

Tyr Thr Gly Tyr Ser Thr His Asn Gly Leu Ser Glu Ser Leu Gly Ile
                85                  90                  95

Gln Asp Ser Asn Val Leu Glu Lys Val Asn Glu Phe Thr Gln Leu Leu
            100                 105                 110

Arg Pro Asp Cys Glu Gly Asn Lys Thr Met Ser Glu Thr Ile Gln Lys
        115                 120                 125

Phe Ser Glu Lys Leu Ala Glu Leu Asp Val Met Val Arg Arg Met Val
    130                 135                 140

Ile Glu Ser Phe Gly Ile Glu Asn Tyr Phe Asp Glu His Leu Lys Ser
145                 150                 155                 160
```

```
Thr Asn Tyr Arg Leu Arg Leu Met Lys Tyr Val Ala Pro Pro Asp Val
            165                 170                 175
Asp Ala Asn Val Ala Val Ser Thr Lys Asp Ser Val Asp Gly Ala Asn
        180                 185                 190
Thr Asn Thr Thr Ala Asn Ala Asp Ala Gly Asp Ile Ala Asn Gly Ile
    195                 200                 205
Ala Lys Val His Ile Asp Asp Ala Asn Ala Lys Gly Asp Val Cys
210                 215                 220
Thr Gly Val Gly Thr Asn His Asn Gly Asp Asp Val Asn Thr Gly Asp
225                 230                 235                 240
Cys Ala Asn Val Lys Ser Asn Val Asp Val Gly Thr Asn Val Ser Ala
                245                 250                 255
Lys Ser Ser Val Gly Ala Asp Val Asn Ile Gly Thr Ile Ala Asp Val
            260                 265                 270
Lys Ala Asn Thr Gly Thr Arg Thr Ser Ala Asn Val Gly Val Ser Asp
        275                 280                 285
Ser Val Lys Ala Asn Gly Gly Ala Asp Asp Glu Glu Lys Lys Leu Gly
    290                 295                 300
Leu Pro Ser His Thr Asp Lys Asn Leu Leu Thr Val Leu Tyr Gln Tyr
305                 310                 315                 320
Glu Ile Glu Gly Leu Glu Val Leu Thr Lys Asp Glu Lys Trp Ile Arg
                325                 330                 335
Leu Lys Pro Ser His Asn Ser Phe Val Val Met Ala Gly Asp Ser Leu
            340                 345                 350
Tyr Ala Leu Met Asn Gly Arg Leu Ser Arg Pro Phe His Arg Val Arg
        355                 360                 365
Val Thr Glu Arg Lys Lys Thr Arg Tyr Ser Ile Ala Leu Phe Ser Thr
    370                 375                 380
Pro Asn Gly Asp Tyr Ile Ile Glu Pro Pro Lys Glu Leu Val Asp Glu
385                 390                 395                 400
Lys His Pro Arg Leu Phe Lys Pro Phe Thr Tyr Val Asp Leu Met Ser
                405                 410                 415
Phe Tyr His Thr Glu Ala Gly Arg Arg Pro Arg Ser Thr Leu His Ala
            420                 425                 430
Tyr Cys Ala Val Ser Gly Ala
        435

<210> SEQ ID NO 5
<211> LENGTH: 5787
<212> TYPE: DNA
<213> ORGANISM: Brassica oleracea (italica group)
<220> FEATURE:
<223> OTHER INFORMATION: genomic BoGSL-ELONG+ allele (plus strand) from
      broccoli

<400> SEQUENCE: 5
cagaaattag catatgtggc ctaccctacc tgggaatgca tacccacgtg atccgttact      60
aataatttag atagcgatat ttaattttaa taaaatacca tgttctaaca actcactttc     120
ttttgaaaga agggtttta actcgcccac ctttttaagca gtattatctt ttaactccca     180
cttaaaaaat attatgatta cattgttgtt cttgtattta catatgaaat cattaaactt     240
acgtcttttt tagaatttac ttgtgtatac tgatacgaaa tcagttcttc tcggatatta     300
ttaatgtaat atgtatacag cggtatatgt atatgtgtaa atatatgaaa taatataaag     360
taaagattaa ttatttgtgt atgatgttaa acacaaaaga gcttccattt acgttcatcg     420
```

-continued

```
ttttaaatta ctacaaaatg atgtaatttt taattttcaa acgcagaaag tatatttaag      480
tcccactatc ataataatta gtattttaat ataaaaactt agaaaataaa agtaaacgat      540
aacaataatt tattttttgc taaaatttgt aacgataata atgccatgaa aaattaagcc      600
atcactccat taaattaaat ggggcttatt gaatttatta agtatctggt tttttaacca      660
aaatcttccc ttattggatt aggtatttat aaaaattatt ttaaatccaa gattgttgga      720
cttatcatct gtataaatcc cactaaccaa tttttagaaa tccattaaaa tggatttttct     780 acccatctat aaatatcgac gaatttttatt gtacatgtta tccatctcat tgcaaaacaa    840
tttcctcact atctttatcc tccaaaccaa tcaaaatatt tatttctctc ctacgtacgt      900
acttcatagt tatggcatcg tcacttctga catcttccgg aattatccct accaccagtt    960
ccaacatggt tgtccggtca ttcttaccct ttggatctgt ccgcctgacc cgtccgtaca   1020
acaagtcgtc cttgctcatc tcatgttgct cctctgtgtc caagaaggct gagactagtg   1080
gtactgacct caaaaccgtt gtggaacggt ggccagagta tattccgaac aagctccccg    1140
acaagaacta cgtgcgtgta tttgatacga cgctccgtga cggcgaacaa tctcccggtg   1200
cagcccttac tccaccgcag aagatagaga ttgcccggca gctcgctaaa ctcagagtag   1260
acatcatgga agttggtttt cccgtgtcat cagaggaaga gttcgaaacc atcaaaacca   1320
tcgccaaaac cgtgggaaac gaggttgttt ctttatttcc ttcttcaaac tatatcgttt   1380
tttttcctaa aaaaactata tcaagtttat ttgataaaga gagtttataa tgaaattcaa     1440
attaaggata attattacgt tgaaagctaa ggggtgtcag tgggaattga attgataatg    1500
actcttagaa ttttcaagtg ggaattgaat tgataatgac tcttagaatt ttgaagtcta   1560
gtgttattgg tttatagatt ctcacattct cattaaaatc tagtgttatt ggtttgatga    1620
ttctataatt ctatacaaaa tcatttatta ttcaattttt tttagatttt aatgattcta   1680
caaatttatt aaagaaatgt tattgaaagt tgaattctta acattttaac tcacaaaaca   1740
agattttgag aatactacat gttttttcttg aattcttaga atcattacat tattttattt    1800
tcatagattt tcacaatata caaaattctc tacaattctt tccaaattta acaaatctct   1860
caacttttaa aatcaacaaa ctctatagaa atctaaagag gtgttgttgg tttatatatt   1920
ttgattgatt tagaaaattca tatagtattt acaaatccaa gtaaaatata cggattttca   1980
aattttctcg gattagtatt tacaaatctg gaggtttttc ctcggatttg agtctttgta    2040
tttttaacaa aaaaactcta tataaatcca ttattaaatt atatctatta ataaatccgc    2100
atggttgaat aacacttgat ttgaattaga atttatagat cataaaatca ataacacttg    2160
atttcaatac ggattttaaa atcatagaac caataacact agatttagtt tagattttca   2220
aatccattaa aatacaccaa ccaataactc ccaccaagtc tcactaacac cccctaagtc   2280
aataagttat ttcaacctca cacaatagtt gttttggtgc caaactttcc cgtatagctg    2340
tggtcaagtg gtatgcaaga ccgagaatgt gttaaaatac tctactcttt ccgtgatctc    2400
gacctcactt gaaacaaatt cacatctatg taaaagtat ggggttgggc tttaatacaa    2460
ttagtttaca tggtactctg gtaaaaggcg attcagcttt ttaacattag tttataaatt    2520
cggatccggc agtgtcgtga ccattcagaa aaaaattact caataaaatt aagtgtgttt    2580
tatcggagtt gactggatta gtcgataaga catataaaat aaatacaccg catgttaatt    2640
ggcatggttt tcatgaaaag catgcatgca caaatgaaga aatggtcaaa gaattagcac    2700
taaaagacta tcgtgtgtga ttgctaggtt gatgaggaaa caggttatat cccagtgata    2760
tgcgtcatcg cacgaagcaa agaaagagat ataaaggcgg cttgggagtc agtgaagtac   2820
```

```
gcaaagaggc cgaggatagt catattcact tctactagtg acattcactt gaaatataag   2880
ttgaaaatga ctagagaaga agtcgtcgag atggtcgcga gtagcattag gtttgctaaa   2940
agtttaggct tcgaagacat cgagtttggt tgcgaagatg gcggcaggtt cacatcttaa   3000
aacctataca tttccattat tattttttt cacaggttca aaagaacata aaattgtggt   3060
actatgtttc tataaagaaa atatttgttg cggtaaaata aaatattaga tccgaatcaa   3120
ccaatggtag cctagtggtc atgcgaaatg aaatcatttc ttagttctca tttagaaaat   3180
ctatgattca gctactcgtc agtttcattt ttttagatga ttaattggac tgcggttcag   3240
acaatcaaag ttgcaaacaa aaacaatatc ggatcggcca atgtaataca tgaatatttc   3300
aaataatgat ggcataatta ctttaaaatg ttattaactg ttgctagata acgttataga   3360
ttttgctgac tttgtaagga actttatata taaaattttc tttttaccat gtcatacatt   3420
attataaaat actaatttgt gattaaaatt aagcaggtcc gacaaggatt atatatgcaa   3480 ggttttttgaa gaagcgatca aagcgggtgc aaccaccctg gcctgccgg acacggtggg    3540 gatcaacatg ccgcacgaat acgggaaact tgtgagatac atcaaagcaa acactcctgg   3600
aattgatgat gttatcttca gcgctcattg tcacaatgac cttggtgttg ctaccgccaa   3660
cacaatcgcc gtaccttttc taatcctgaa attttgttca tttatttaca aatatcaatt   3720
caaaatacat aaataacaat gagtttacac attatgtata aataaacagg gtatatgtgc   3780
gggagcacga caagtcgaag taacaatcaa tggaataggt gaagaagtg ggaatgcacc    3840 gcttgaagag gtaagaactg ctagaaatcc acttccaaag tgagatagaa cataagatag   3900
tacaactgat atgaatcgat ctattactca ttttgttgcg agttggtttt gaaacagtc    3960 caagaaagtc aacaagctcg taatggttta ttatcatcaa ttcatcatca agatgaatat   4020
ttatttggta tatataggtc gtgatggctt tgaaatgtcg aggagcattt gtgatgggtg   4080
gtgtttacac aagaatagac acacgccaaa ttatggctac cagcaagatg gtaactttga   4140
catgtcgagg agctagtgtt ttctatccta agcgtttata ataattgact aatagttgct   4200
aattcttgag caggttcaag aatatactgg cttgtatgtt cagccacata aacctatagt   4260
tggagccaac tgttttgttc atgagagcgg cattcaccag gttcggtgca tatatataca   4320
tgcataacta cttatattat acagaaagtc agttatgaga ttgatttggt tatcattctt   4380
tacacatttt gaaggatggg atattgaaaa atcggagtac atatgagatc ttatcaccag   4440
aagatgttgg agttgtgaaa tctcaaaatt caggcattgt tcttggaaag cttaggtaat   4500
tattcaattt taagtaatat tattcaattt tgaagtaata ttttagtggt tttactaatg   4560
aaattacggg acgtaccatt ttaactcgtt tgtataacta tggaactatg tagtggacgt   4620
catgcggtta aaggtcgtct gaaagaggta cataccttgt aatttaatca tatatgtact   4680
cgttggttac acaactatca tatataaata ctcaaataag agatctatgt atttattcat   4740
taacatactt gaatatctat ttctgctctc agttgggata tgaaatcagt gatgagaaac   4800
tgaacgaggt tttctcacgg ttcagagatt taaccaagca gaaaaaggtt ttgtttttaa   4860
ttttctatat atatatatat atatatatat ataatatcct gtgcacatat gcttatgata   4920
tagcttatat actaagtata tttgatataa gaattttaaa tacgaattgc ttatgaaatc   4980
tcacacttaa gtatggggtt gggtttcata ttgttgataa tttcagagag tcacggatga   5040
tgatctaagg gcattagtaa cgtgtggtga tgaaatcttc tcctcagaga aattaaacgg   5100
cactaacgac aacgaaatca acagaaacgg ctatgtaccg tctcctcaga tttcctctgt   5160
```

-continued

```
ggtatgaatt atgtgaccac gtctgttatg tttgtgtatc actgtaatat caagtttctt    5220
ttgaaacttg taatgaataa aacaagtttc ttttcctcta aagatgaaaa gcttaagcat    5280
taatcacttg cctgggaggt gcaaaaggtt ccaattgtca cccatctatc gaacagagta    5340
tattagggtt ggtaatgggc taaatatatt gagatatata tactctcgta tattctctat    5400
atcattagct atataagacc atcattaacg gtaaagggct cttagggttt ttttttttctt   5460 tttttttgtct gatttaaaaa aaacaaatta aaaacgaatc aatcgcgggc tgtcacatgt   5520
cagtggggcc cgtaaaaagt ggcaaaaccc tctcaaactc gactcttact gaaaaagtag    5580
aagaggcagc ccttagaatt taggtgggat ccgcatgatt ttaaattttt tttttttaagg   5640 ggcaacttta ataggcgccg ttgttgatgc tctaactttt ttttttttgta acaccaatac   5700 tttcatttaa ttaaaggcct cagacccaaa cgatgtctga acagaaatg aaaacttaag    5760 aaagctgaaa agagataaat ttaagct                                        5787
```

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:me1 forward
      primer

<400> SEQUENCE: 6
tgagtccaaa ccggata                                                    17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:me2 forward
      primer

<400> SEQUENCE: 7
tgagtccaaa ccggagc                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:me3 forward
      primer

<400> SEQUENCE: 8
tgagtccaaa ccggaat                                                    17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:me4 forward
      primer

<400> SEQUENCE: 9
tgagtccaaa ccggacc                                                    17

<210> SEQ ID NO 10
<211> LENGTH: 17
<212> TYPE: DNA
<213> ORGANISM: Artificial Sequence

```
-continued

<220> FEATURE:
<223> OTHER INFORMATION: Description of Artificial Sequence:me5 forward
      primer

<400> SEQUENCE: 10
tgagtccaaa ccggaag                                                    17

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:em1 reverse
      primer

<400> SEQUENCE: 11
gactgcgtac gaattaat                                                   18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:em2 reverse
      primer

<400> SEQUENCE: 12
gactgcgtac gaatttgc                                                   18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:em3 reverse
      primer

<400> SEQUENCE: 13
gactgcgtac gaattgac                                                   18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:em4 reverse
      primer

<400> SEQUENCE: 14
gactgcgtac gaatttga                                                   18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:em5 reverse
      primer

<400> SEQUENCE: 15
gactgcgtac gaattaac                                                   18

<210> SEQ ID NO 16
<211> LENGTH: 18
<212> TYPE: DNA
<213> ORGANISM: Artificial Sequence
<220> FEATURE:
```

```
<223> OTHER INFORMATION: Description of Artificial Sequence:em6 reverse
      primer

<400> SEQUENCE: 16
gactgcgtac gaattgca                                                        18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:marker
      Sequence-Related Amplified Polymorphism (SRAP) 133
      primer FC1

<400> SEQUENCE: 17
gtcaagggca ggtaagaaca a                                                    21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:marker
      Sequence-Related Amplified Polymorphism (SRAP) 133
      primer FC2

<400> SEQUENCE: 18
gcattgacgg ttaccttgat                                                      20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:BoGSL-ALK
      primer ODD48

<400> SEQUENCE: 19
ttccatcatt tactttctca g                                                    21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:BoGSL-ALK
      primer ODD49

<400> SEQUENCE: 20
aagccggtcc taatttgtaa                                                      20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:BoGSL-ALK+
      allele marker assisted selection primer FC7

<400> SEQUENCE: 21
atgtgttgat tctgccgag                                                       19

<210> SEQ ID NO 22
<211> LENGTH: 19
<212> TYPE: DNA
<213> ORGANISM: Artificial Sequence
```

```
<220> FEATURE:
<223> OTHER INFORMATION: Description of Artificial Sequence:BoGSL-ALK+
      allele marker assisted selection primer FC8

<400> SEQUENCE: 22
gtgctttact gtttgctcc                                                 19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:GSL-ELONG
      PCR amplification primer IPM2

<400> SEQUENCE: 23
gtgacggtga acaatctcct                                                20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:BoGSL-ELONG
      allele marker assisted selection and PCR
      amplification primer IPM9

<400> SEQUENCE: 24
gtagtattct caaaatcttg t                                              21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:BoGSL-PRO-
      allele dominant marker amplification primer Ce6

<400> SEQUENCE: 25
cgaattttag ggtatccata                                                20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:BoGSL-PRO-
      allele dominant marker amplification primer Ce7

<400> SEQUENCE: 26
gtactgcatg gagtgagaa                                                 19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:
      amplification primer Ce39 for co-dominant microsatellite (SSR)
      markers for BoGSL-PRO alleles

<400> SEQUENCE: 27
gaatgtccta aaatcaatac t                                              21

<210> SEQ ID NO 28
<211> LENGTH: 20
<212> TYPE: DNA
```

```
<213> ORGANISM: Artificial Sequence
<220> FEATURE:
<223> OTHER INFORMATION: Description of Artificial Sequence:
      amplification primer Ce40 for co-dominant microsatellite (SSR)
      markers for BoGSL-PRO alleles

<400> SEQUENCE: 28
ttttcactag cgttccaatt                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      amplification primer ODD14 for co-dominant microsatellite marker
      for marker assisted selection of BoGSL-ALK alleles

<400> SEQUENCE: 29
tcggtctttg tcgttttcta                                              20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:
      amplification primer ODD15 for co-dominant microsatellite marker
      for marker assistedselection of BoGSL-ALK alleles

<400> SEQUENCE: 30
gcgaggatgc tactggtt                                                18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:BoGSL-ELONG
      allele marker assisted selection and PCR
      amplification primer IPM1

<400> SEQUENCE: 31
gccatcttcg cacccaaa                                                18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:BoGLS-ELONG
      RT-PCR exon 3 primer

<400> SEQUENCE: 32
aagcgatcaa agcgggtg                                                18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:BoGLS-ELONG
      RT-PCR exon 4 primer

<400> SEQUENCE: 33
cttcaagcgg tgcattcc                                                18
```

<210> SEQ ID NO 34
<211> LENGTH: 1464
<212> TYPE: DNA
<213> ORGANISM: Brassica oleracea (italica group)
<220> FEATURE:
<223> OTHER INFORMATION: BoGSL-ELONG coding sequence from broccoli

<400> SEQUENCE: 34

| | | | | | |
|---|---|---|---|---|---|
| atggttgtcc | ggtcattctt | acccttggga | tctgtccgcc | tgacccgtcc | gtacaacaag | 60 |
| tcgtccttgc | tcatctcatg | ttgctcctct | gtgtccaaga | aggctgagac | tagtggtact | 120 |
| gacctcaaaa | ccgttgtgga | acggtggcca | gagtatattc | cgaacaagct | ccccgacaag | 180 |
| aactacgtgc | gtgtatttga | tacgacgctc | cgtgacggcg | aacaatctcc | cggtgcagcc | 240 |
| cttactccac | cgcagaagat | agagattgcc | cggcagctcg | ctaaactcag | agtagacatc | 300 |
| atggaagttg | gttttcccgt | gtcatcagag | gaagagttcg | aaaccatcaa | aaccatcgcc | 360 |
| aaaccgtgg | gaaacgaggt | tgatgaggaa | acaggttata | tcccagtgat | atgcgtcatc | 420 |
| gcacgaagca | agaaagaga | tataaaggcg | gcttgggagt | cagtgaagta | cgcaaagagg | 480 |
| ccgaggatag | tcatattcac | ttctactagt | gacattcact | tgaaatataa | gttgaaaatg | 540 |
| actagagaag | aagtcgtcga | gatggtcgcg | agtagcatta | ggtttgctaa | aagtttaggc | 600 |
| ttcgaagaca | tcgagtttgg | ttgcgaagat | ggcggcaggt | ccgacaagga | ttatatatgc | 660 |
| aaggttttg | aagaagcgat | caaagcgggt | gcaaccaccc | tggcctgccc | ggacacggtg | 720 |
| gggatcaaca | tgccgcacga | atacgggaaa | cttgtgagat | acatcaaagc | aaacactcct | 780 |
| ggaattgatg | atgttatctt | cagcgctcat | tgtcacaatg | accttggtgt | tgctaccgcc | 840 |
| aacacaatcg | ccggtatatg | tgcgggagca | cgacaagtcg | aagtaacaat | caatggaata | 900 |
| ggtgaaagaa | gtgggaatgc | accgcttgaa | gaggtcgtga | tggctttgaa | atgtcgagga | 960 |
| gcatttgtga | tgggtggtgt | ttacacaaga | atagacacac | gccaaattat | ggctaccagc | 1020 |
| aagatggttc | aagaatatac | tggcttgtat | gttcagccac | ataaacctat | agttggagcc | 1080 |
| aactgttttg | ttcatgagag | cggcattcac | caggatggga | tattgaaaaa | tcggagtaca | 1140 |
| tatgagatct | tatcaccaga | agatgttgga | gttgtgaaat | ctcaaaattc | aggcattgtt | 1200 |
| cttggaaagc | ttagtggacg | tcatgcggtt | aaaggtcgtc | tgaaagagtt | gggatatgaa | 1260 |
| atcagtgatg | agaaactgaa | cgaggttttc | tcacggttca | gagatttaac | caagcagaaa | 1320 |
| aagagagtca | cggatgatga | tctaagggca | ttagtaacgt | gtggtgatga | aatcttctcc | 1380 |
| tcagagaaat | taacggcac | taacgacaac | gaaatcaaca | gaaacggcta | tgtaccgtct | 1440 |
| cctcagattt | cctctgtggt | atga | | | | 1464 |

<210> SEQ ID NO 35
<211> LENGTH: 487
<212> TYPE: PRT
<213> ORGANISM: Brassica oleracea (italica group)
<220> FEATURE:
<223> OTHER INFORMATION: BoGSL-ELONG from broccoli

<400> SEQUENCE: 35

Met Val Val Arg Ser Phe Leu Pro Phe Gly Ser Val Arg Leu Thr Arg
 1               5                  10                  15

Pro Tyr Asn Lys Ser Ser Leu Leu Ile Ser Cys Cys Ser Ser Val Ser
            20                  25                  30

Lys Lys Ala Glu Thr Ser Gly Thr Asp Leu Lys Thr Val Val Glu Arg
        35                  40                  45

Trp Pro Glu Tyr Ile Pro Asn Lys Leu Pro Asp Lys Asn Tyr Val Arg

```
            50                  55                  60
Val Phe Asp Thr Thr Leu Arg Asp Gly Glu Gln Ser Pro Gly Ala Ala
 65                  70                  75                  80

Leu Thr Pro Pro Gln Lys Ile Glu Ile Ala Arg Gln Leu Ala Lys Leu
                 85                  90                  95

Arg Val Asp Ile Met Glu Val Gly Phe Pro Val Ser Ser Glu Glu Glu
                100                 105                 110

Phe Glu Thr Ile Lys Thr Ile Ala Lys Thr Val Gly Asn Glu Val Asp
                115                 120                 125

Glu Glu Thr Gly Tyr Ile Pro Val Ile Cys Val Ile Ala Arg Ser Lys
130                 135                 140

Glu Arg Asp Ile Lys Ala Ala Trp Glu Ser Val Lys Tyr Ala Lys Arg
145                 150                 155                 160

Pro Arg Ile Val Ile Phe Thr Ser Thr Ser Asp Ile His Leu Lys Tyr
                165                 170                 175

Lys Leu Lys Met Thr Arg Glu Glu Val Val Glu Met Val Ala Ser Ser
                180                 185                 190

Ile Arg Phe Ala Lys Ser Leu Gly Phe Glu Asp Ile Glu Phe Gly Cys
                195                 200                 205

Glu Asp Gly Gly Arg Ser Asp Lys Asp Tyr Ile Cys Lys Val Phe Glu
                210                 215                 220

Glu Ala Ile Lys Ala Gly Ala Thr Thr Leu Ala Cys Pro Asp Thr Val
225                 230                 235                 240

Gly Ile Asn Met Pro His Glu Tyr Gly Lys Leu Val Arg Tyr Ile Lys
                245                 250                 255

Ala Asn Thr Pro Gly Ile Asp Asp Val Ile Phe Ser Ala His Cys His
                260                 265                 270

Asn Asp Leu Gly Val Ala Thr Ala Asn Thr Ile Ala Gly Ile Cys Ala
                275                 280                 285

Gly Ala Arg Gln Val Glu Val Thr Ile Asn Gly Ile Gly Glu Arg Ser
                290                 295                 300

Gly Asn Ala Pro Leu Glu Glu Val Val Met Ala Leu Lys Cys Arg Gly
305                 310                 315                 320

Ala Phe Val Met Gly Gly Val Tyr Thr Arg Ile Asp Thr Arg Gln Ile
                325                 330                 335

Met Ala Thr Ser Lys Met Val Gln Glu Tyr Thr Gly Leu Tyr Val Gln
                340                 345                 350

Pro His Lys Pro Ile Val Gly Ala Asn Cys Phe Val His Glu Ser Gly
                355                 360                 365

Ile His Gln Asp Gly Ile Leu Lys Asn Arg Ser Thr Tyr Glu Ile Leu
                370                 375                 380

Ser Pro Glu Asp Val Gly Val Lys Ser Gln Asn Ser Gly Ile Val
385                 390                 395                 400

Leu Gly Lys Leu Ser Gly Arg His Ala Val Lys Gly Arg Leu Lys Glu
                405                 410                 415

Leu Gly Tyr Glu Ile Ser Asp Glu Lys Leu Asn Glu Val Phe Ser Arg
                420                 425                 430

Phe Arg Asp Leu Thr Lys Gln Lys Lys Arg Val Thr Asp Asp Asp Leu
                435                 440                 445

Arg Ala Leu Val Thr Cys Gly Asp Glu Ile Phe Ser Ser Glu Lys Leu
450                 455                 460

Asn Gly Thr Asn Asp Asn Glu Ile Asn Arg Asn Gly Tyr Val Pro Ser
465                 470                 475                 480
```

Pro Gln Ile Ser Ser Val Val
                485

<210> SEQ ID NO 36
<211> LENGTH: 3077
<212> TYPE: DNA
<213> ORGANISM: Brassica oleracea (italica group)
<220> FEATURE:
<223> OTHER INFORMATION: genomic BoGSL-PRO+ allele (plus strand) from
      broccoli
<220> FEATURE:
<221> NAME/KEY: modified_base
<222> LOCATION: (9)
<223> OTHER INFORMATION: n = g, a, c or t

<400> SEQUENCE: 36

| | | | | | |
|---|---|---|---|---|---|
| tccggttcng | agaaaccta | atgctctcat | cacaacaaca | atcaccaccc | ttctcttccc | 60 |
| tccttctcct | cgaaacctca | cctctctcat | tccgcttccc | accctcccac | caccgctcct | 120 |
| ctctccgcat | caaatccctc | cgcctctcgt | gctccctctc | agatccctct | cctcccctcc | 180 |
| gccgctgccg | cccggagtac | atccccaacc | gcatttccga | ccccaactac | gtccgagtct | 240 |
| tcgacaccac | tctccgcgac | ggcgaacagt | cccccggagc | caccctcacc | tccaaagaga | 300 |
| agctcgacat | cgcgcgccag | ctcgcgaagc | tgggcgtcga | cgtaatcgag | gccgggttcc | 360 |
| ccgccgcctc | caaggacgac | ttcgaagccg | tgaaaaccat | agccgaaacc | gtgggaaacg | 420 |
| ccgtcgacgg | agacggttac | gtccccgtca | tctgcggact | ctcgagatgc | aacaagagag | 480 |
| atatcgagac | ggcgtgggag | gctgtgaagt | acgccaaaag | gccgaggatc | catacctca | 540 |
| tcgccacgag | tgacattcac | ttggagtata | agctgaagaa | gagcaaagac | gaggtcatcg | 600 |
| agatcgctag | gaatatggta | aagttcgcga | ggagcttggg | gtgtgaggac | gttgagttta | 660 |
| gtcctgaaga | tgccggaagg | ttcgagattt | ttttgctttt | tgtgaataag | agaatcttct | 720 |
| tattgtttga | ttctttttt | cttttttgga | ttttttctaga | tcggagagag | agttttttgta | 780 |
| tcagattctt | ggggaagtga | taaaagctgg | agcgacaacg | cttaatatac | ctgacactgt | 840 |
| tggtataacg | ttgcctagtg | agtttggtca | gttgattgct | gatatcaaag | ccaatactcc | 900 |
| tgggatcgag | aatgttatca | tctcaacgca | ttgtcagaat | gatcttgggc | tctccactgc | 960 |
| caacacttta | tctgtattgt | caacttttct | ttctcctttc | ggcttagatc | agattagctt | 1020 |
| agctctcaga | atgttctcag | tcacatcgtt | tttggttatt | cagggtgcac | attcgggtgc | 1080 |
| aaggcaagtg | gaagtgacta | tcaatggcat | tggcgaaaga | gctggaaacg | cttcactaga | 1140 |
| agaggttaga | ttttgttgca | ttcaattcat | gatcatctag | tgttgcattt | gaatacttat | 1200 |
| tttattacct | aaagattgtc | tttgtaactg | tttaggttgt | gatggccata | aaatgccgtg | 1260 |
| gagatcatgt | acttggaggc | ctatatactg | gaattgatac | tcggcacatt | gttatgacaa | 1320 |
| gcaagatggt | atacttttaa | acgttgttta | cgctgtgaag | acaaactagt | tttcttgtct | 1380 |
| tgagaagggg | aaaagagtat | gtagatttgc | taagataagg | tgtctcataa | cgtgtggctt | 1440 |
| gatttatcag | gttgaagatt | acacaggaat | gcaaacacag | ccccataagg | ctattgtagg | 1500 |
| agcgaatgcc | tttgcgcatg | aaagtggtat | tcatcaggtc | agttgatgaa | ataaatcgtt | 1560 |
| gtaatatgta | ttttgattac | tcttttgat | aaatattaaa | ggttgttcac | atgatctatc | 1620 |
| tttccccctt | ttttgcaaag | tataactttc | cttgtaggct | gtaaacttta | agctatatac | 1680 |
| tcttttgact | tgcatgttca | ctctttcttg | tacaactatc | tacatgattg | tttctccagt | 1740 |
| tgcgcttaat | gactgttcat | acttcttta | ggatggaatg | ctcaaacaca | agggcacata | 1800 |

-continued

```
tgaaattata tgccccgaag aaattggact tgaacgatct aatgatgctg gtattgtttt    1860
ggggaagctt aggtatgtaa gcttttctt gtatagacaa tgcaacaagc cgacacgcct     1920
gtaactggtg gatatactct acagttagga taatttgctt ttgacgttga atatttccag    1980
acactactag gcatttggtt ttatttgaca acttagcaat tcataagcta ctgtacacta    2040
cgtatatact tgaaacctga agtctaactg ttggcttctg ttttgcttgg atatgcagtg    2100
ggcgtcatgc gttgaaagac cgtttgactg aggtacacat caatctttac ccaaacacat    2160
actcactatt gccatctttg tgggagacac taatgtcctt ttgtattttt gtattaccag    2220
cttggttatg tactagatga tgaacaacta agttccattt tctggcgctt caaatctgtg    2280
gctgagcgga aaaggtagt tggttttata tgcgttattc attcaaactt atagttttca     2340
atcccaactg atgtatgtgt tattttcatg atccagagag ttaccgacgc agatataata    2400
gctttggttt ctgatgaggt tttccagcca gaagctctgt ggaaactcct ggacattcag    2460
gtgaaactgg gatcaagatg atctttcttt tactcgtttt cttactcaat tgtctttagt    2520
caattctcat tttagttgaa actggaatgc agataacttg tgggactttg gggctttcaa    2580
cagcaaccgt gaaacttgct gacgctgatg gcaaagagca tgttgcttgt tctatgggaa    2640
ccgggcctgt cgattcagca tataaggcag tcgatcttat tgtcaaggta ttaatatatt    2700
atacaattgt ggctgatata tacatataac ttcacctta tatcatcggt tatttaaaaa     2760
acttcatttt ccacattgta ggaaccagcg actctgcttg agtactcaat gaatgcagta    2820
acagaaggca tcgatgccat tgcaaccaca agagttctta tccgaggaaa caacaattac    2880
tcaactacaa acgcaatcac tggtgaagaa gttcaaagga cctttaggta aaaaatcgtc    2940
ttccctcata tctaattcaa cttataccca gcttatttt attgcctttc tgattatttt     3000
ataacacgga acgagtctgt cttttggcag tggaaccgga gcaggaatgg acatcgtggt    3060
gtcaagcgtc aaagcaa                                                   3077
```

<210> SEQ ID NO 37
<211> LENGTH: 410
<212> TYPE: PRT
<213> ORGANISM: Arabidopsis thaliana
<220> FEATURE:
<223> OTHER INFORMATION: 2-oxoglutarate-dependent dioxygenase (ODD) 3
    from ecotype Cape Verde Islands (Atcvi3)

<400> SEQUENCE: 37

```
Met Gly Ser Cys Ser Pro Gln Leu Pro Leu Ile Cys Leu Ser Asp Gln
  1               5                  10                  15

Thr Leu Lys Pro Gly Ser Ser Lys Trp Val Lys Val Arg Ser Asp Val
             20                  25                  30

Arg Lys Ala Leu Glu Asp Tyr Gly Cys Phe Glu Ala Lys Ile Asp Gln
         35                  40                  45

Val Ser Met Glu Leu Gln Gly Ser Val Leu Lys Ala Met Gln Glu Leu
     50                  55                  60

Phe Ala Leu Pro Thr Glu Ala Lys Gln Arg Asn Val Cys Pro Lys Pro
 65                  70                  75                  80

Phe Ala Gly Tyr Phe Ser His Asn Gly Ser Leu Glu Ser Phe Gly Ile
                 85                  90                  95

Lys Asp Ala Asn Ile Leu Glu Lys Ala His Glu Phe Thr Gln Gln Leu
            100                 105                 110

Trp Pro Glu Gly Asn Lys Ser Ile Lys Met Ile Gln Leu Tyr Ala Glu
        115                 120                 125
```

```
Lys Leu Ala Glu Leu Asp Met Met Val Arg Arg Leu Ile Leu Glu Ser
            130                 135                 140

Tyr Gly Ile Glu Tyr Phe Ile Asp Glu His Leu Asn Ser Thr Tyr Tyr
145                 150                 155                 160

Arg Met Arg Leu Met Lys Tyr Ile Ala Arg Pro Asp Asn Asp Ile Thr
                165                 170                 175

Ala Ala Val Gly Ala Asn Val Asp Asn Gly Ala Asn Asp Asn Ala Asp
            180                 185                 190

Gly Asp Ala Asn Val Asn Asp Asp Gly Ala Ser Ile Gly Val Lys Val
                195                 200                 205

Asn Val Asp Val Gly Asp Asp Val Asn Asp Asn Asp Ser Val Asn Ile
210                 215                 220

Gly Val Gly Val Asp Ile Asn Val Glu Thr Asn Val Asn Gly His Leu
225                 230                 235                 240

Asp Ala Glu Ala Asn Gly Asp Ala Thr Ala Trp Val Val Gly Ala Val
                245                 250                 255

Ser Gly Asn Ala Ser Val Gly Ala Lys Glu Ala Asn Val Asp Ala Glu
                260                 265                 270

Leu Gly Leu Pro Ser His Thr Asp Lys Ser Leu Ser Gly Ile Ile Tyr
                275                 280                 285

Gln His Gln Ile Asp Gly Leu Glu Val Lys Thr Lys Glu Gly Lys Trp
290                 295                 300

Ile Arg Val Lys Pro Ala Pro Asn Thr Val Ile Phe Ile Ala Gly Asp
305                 310                 315                 320

Ala Leu Cys Ala Leu Met Asn Gly Arg Ile Pro Ser Pro Tyr His Arg
                325                 330                 335

Val Arg Val Thr Glu Lys Lys Lys Thr Arg Tyr Ala Ala Ala Leu Phe
                340                 345                 350

Ser Asn Pro Lys Glu Gly Tyr Ile Ile Asp Ser Pro Lys Glu Leu Val
                355                 360                 365

Asp Glu Lys His Pro Arg Ala Phe Lys Pro Phe Asp Phe Val Asp Leu
            370                 375                 380

Phe Asn Phe Tyr His Thr Glu Ala Gly Arg Arg Ala Pro Ser Thr Leu
385                 390                 395                 400

Gln Ala Phe Cys Gly Val Ser Ala Gly Lys
                405                 410
```

<210> SEQ ID NO 38
<211> LENGTH: 410
<212> TYPE: PRT
<213> ORGANISM: Arabidopsis thaliana
<220> FEATURE:
<223> OTHER INFORMATION: 2-oxoglutarate-dependent dioxygenase (ODD) 3
      from ecotype Landsberg (Atler3)

<400> SEQUENCE: 38

```
Met Gly Ser Cys Ser Pro Gln Leu Pro Leu Ile Cys Leu Ser Asp Gln
 1               5                  10                  15

Thr Leu Lys Pro Gly Ser Ser Lys Trp Val Lys Val Arg Ser Asp Val
                20                  25                  30

Arg Lys Ala Leu Glu Asp Tyr Gly Cys Phe Glu Ala Lys Ile Asp Gln
            35                  40                  45

Val Ser Met Glu Leu Gln Gly Ser Val Leu Lys Ala Met Gln Glu Leu
        50                  55                  60

Phe Ala Leu Pro Thr Glu Ala Lys Gln Arg Asn Val Cys Pro Lys Pro
65                  70                  75                  80
```

```
Phe Ala Gly Tyr Phe Ser His Asn Gly Ser Leu Glu Ser Phe Gly Ile
                 85                  90                  95

Lys Asp Ala Asn Ile Leu Glu Lys Ala His Glu Phe Thr Gln Gln Leu
            100                 105                 110

Trp Pro Glu Gly Asn Lys Ser Ile Lys Met Ile Gln Leu Tyr Ala Glu
            115                 120                 125

Lys Leu Ala Glu Leu Asp Met Met Val Arg Arg Leu Ile Leu Glu Ser
130                 135                 140

Tyr Gly Ile Glu Tyr Phe Ile Asp Glu His Leu Asn Ser Thr Tyr Tyr
145                 150                 155                 160

Arg Met Arg Leu Met Lys Tyr Ile Ala Arg Pro Asp Asn Asp Ile Thr
                165                 170                 175

Ala Ala Val Gly Ala Asn Val Asp Asn Gly Ala Asn Asp Asn Ala Asp
            180                 185                 190

Gly Asp Ala Asn Val Asn Asp Asp Gly Ala Ser Ile Gly Val Lys Val
            195                 200                 205

Asn Val Asp Val Gly Asp Asp Val Asn Asp Asn Asp Ser Val Asn Ile
210                 215                 220

Gly Val Gly Val Asp Ile Asn Val Glu Thr Asn Val Asn Gly Asp Leu
225                 230                 235                 240

Asp Ala Glu Ala Asn Gly Asp Ala Thr Ala Trp Val Val Gly Ala Val
                245                 250                 255

Ser Gly Asn Ala Ser Val Gly Ala Lys Glu Ala Asn Val Asp Ala Glu
            260                 265                 270

Leu Gly Leu Pro Ser His Thr Asp Lys Ser Leu Ser Gly Ile Ile Tyr
            275                 280                 285

Gln His Gln Ile Asp Gly Leu Glu Val Lys Thr Lys Glu Gly Lys Trp
290                 295                 300

Ile Arg Val Lys Pro Ala Pro Asn Thr Val Ile Val Ile Ala Gly Asp
305                 310                 315                 320

Ala Leu Cys Ala Leu Met Asn Gly Arg Ile Pro Ser Pro Tyr His Arg
                325                 330                 335

Val Arg Val Thr Glu Arg Lys Lys Thr Arg Tyr Ala Ala Ala Leu Phe
            340                 345                 350

Ser Tyr Pro Lys Glu Gly Tyr Ile Ile Asp Ser Pro Lys Glu Leu Val
            355                 360                 365

Asp Glu Lys His Pro Arg Ala Phe Lys Pro Phe Asp Phe Val Asp Leu
370                 375                 380

Phe Asn Phe Tyr His Thr Glu Ala Gly Arg Arg Ala Pro Ser Thr Leu
385                 390                 395                 400

Gln Ala Phe Cys Gly Val Ser Ala Gly Lys
                405                 410

<210> SEQ ID NO 39
<211> LENGTH: 432
<212> TYPE: PRT
<213> ORGANISM: Arabidopsis thaliana
<220> FEATURE:
<223> OTHER INFORMATION: 2-oxoglutarate-dependent dioxygenase (ODD) 2
      from ecotype Cape Verde Islands (Atcvi2)

<400> SEQUENCE: 39

Met Gly Ser Cys Ser Leu Gln Leu Pro Leu Ile Asn Leu Ala Asp Lys
 1               5                  10                  15

Thr Leu Glu Pro Gly Ser Ser Lys Trp Ala Glu Val Arg Ser Asp Val
```

```
                    20                  25                  30
Arg Lys Ala Leu Glu Asp Phe Gly Cys Phe Glu Ala Ser Tyr Asp Lys
         35                  40                  45
Val Ser Leu Glu Leu Gln Glu Ser Ile Met Lys Thr Met Glu Glu Leu
     50                  55                  60
Phe Ala Leu Pro Val Glu Thr Lys Gln Arg Asn Val Cys Pro Lys Pro
 65                  70                  75                  80
Tyr Val Gly Tyr Leu Asn His Asn Asn Leu Ser Glu Ser Leu Gly Ile
                 85                  90                  95
Ser Asn Ala Asn Ile Leu Glu Asn Val Asn Glu Phe Thr Gln Gln Leu
             100                 105                 110
Trp Pro Asp Gly Asp Gly Asn Glu Asn Ile Ser Lys Thr Ile Gln Leu
         115                 120                 125
Phe Ala Glu Lys Leu Val Glu Ile Asp Val Met Val Arg Arg Met Val
     130                 135                 140
Met Glu Ser Phe Gly Ile Glu Lys Tyr Ile Asp Asp His Leu Lys Ser
145                 150                 155                 160
Thr Glu Tyr Arg Met Arg Leu Met Lys Tyr Ile Ala Pro Pro Glu Gly
                 165                 170                 175
Asp Ala Asn Thr Thr Val Asp Asp Tyr Ala Asp Leu Leu Ala Lys Leu
             180                 185                 190
Asn Ile Asp Gly Val Glu Pro Asn Val Gly Val Lys Val Asn Ala Asp
         195                 200                 205
Ile Ser Asp Asp Val Asn Ala Asn Pro Ser Val Asn Ala Gly Val Gly
     210                 215                 220
Ala Asn Val Asn Ala Asp Thr Gly Val Asn Asp Asn Leu Asn Val Asp
225                 230                 235                 240
Ala Glu Ala Asn Gly Asp Ala Asn Ile Ala Val Gly Gly Gly Val Asn
                 245                 250                 255
Ala Asn Thr Asp Leu Gly Val Gly Val Asn Val Asn Ser Asn Val Ala
             260                 265                 270
Val Asn Ala Lys Thr Gly Ala Thr Ser Gly Asp Asp Val Glu Ala Asn
         275                 280                 285
Asp Asp Asn Glu Glu Lys Lys Leu Gly Leu Pro Cys His Thr Asp Lys
     290                 295                 300
Asn Leu Phe Thr Val Leu Phe Gln His Glu Ile Glu Gly Leu Glu Val
305                 310                 315                 320
Lys Thr Lys Asp Glu Lys Trp Ile Arg Val Lys Pro Ser Pro Asn Thr
                 325                 330                 335
Phe Ile Val Ile Ala Gly Asp Ser Leu Cys Ala Leu Met Asn Gly Arg
             340                 345                 350
Ile Arg Ala Pro Tyr His Arg Val Arg Val Thr Glu Lys Lys Arg Thr
         355                 360                 365
Arg Tyr Thr Ala Ala Ile Phe Thr Cys Pro Lys Pro Asp Tyr Val Ile
     370                 375                 380
Glu Ala Pro Lys Glu Leu Val Asp Glu Lys His Pro Arg Leu Phe Arg
385                 390                 395                 400
Pro Phe Asp Tyr Arg Asp Leu Phe Thr Phe Tyr His Ser Glu Ala Gly
                 405                 410                 415
Arg Lys Ile Gln Tyr Thr Leu Gln Ala Tyr Cys Ala Val Ser Glu Ala
             420                 425                 430

<210> SEQ ID NO 40
```

<211> LENGTH: 439
<212> TYPE: PRT
<213> ORGANISM: Brassica oleracea
<220> FEATURE:
<223> OTHER INFORMATION: BoGSL-ALK from collard

<400> SEQUENCE: 40

```
Met Gly Ala Asp Thr Pro Gln Leu Pro Val Ile Tyr Leu Ser Asp Gln
 1               5                  10                  15

Thr Leu Lys Pro Gly Ser Glu Lys Trp Val Glu Val Arg Ser Asp Val
            20                  25                  30

Arg Lys Ala Leu Glu Asp Tyr Gly Ala Phe Glu Val Ser Tyr Asp Arg
        35                  40                  45

Val Ser Glu Glu Leu Lys Lys Ser Val Leu Asp Ala Met Ile Glu Leu
    50                  55                  60

Phe Glu Leu Pro Val Glu Ala Lys Gln Arg Asn Val Ser Pro Lys Pro
65                  70                  75                  80

Tyr Thr Gly Tyr Ser Thr His Asn Gly Ser Leu Glu Ser Leu Gly Ile
                85                  90                  95

Gln Asp Ser Asn Val Leu Glu Lys Val Asn Glu Phe Thr Gln Leu Leu
            100                 105                 110

Arg Pro Asp Cys Glu Gly Asn Lys Thr Met Ser Glu Thr Ile Gln Lys
        115                 120                 125

Phe Ser Glu Lys Leu Ala Glu Leu Asp Val Met Val Arg Arg Met Val
    130                 135                 140

Ile Glu Ser Phe Gly Ile Glu Asn Tyr Phe Asp Glu His Leu Lys Ser
145                 150                 155                 160

Thr Asn Tyr Arg Leu Arg Leu Met Lys Tyr Val Ala Pro Pro Asp Val
                165                 170                 175

Asp Ala Asn Val Ala Val Ser Thr Lys Asp Ser Val Asp Gly Ala Asn
            180                 185                 190

Thr Asn Thr Thr Ala Asn Ala Asp Ala Gly Asp Ile Ala Asn Gly Ile
        195                 200                 205

Ala Lys Val His Ile Asp Asp Ala Asn Ala Lys Gly Asp Val Cys
    210                 215                 220

Thr Gly Val Gly Thr Asn His Asn Gly Asp Asp Val Asn Thr Gly Asp
225                 230                 235                 240

Cys Ala Asn Val Lys Ser Asn Val Asp Val Gly Thr Asn Val Ser Ala
                245                 250                 255

Lys Ser Ser Val Gly Ala Asp Val Asn Ile Gly Thr Ile Ala Asp Val
            260                 265                 270

Lys Ala Asn Thr Gly Thr Arg Thr Ser Ala Asn Val Gly Val Ser Asp
        275                 280                 285

Ser Val Lys Ala Asn Gly Gly Ala Asp Asp Glu Glu Lys Lys Leu Gly
    290                 295                 300

Leu Pro Ser His Thr Asp Lys Asn Leu Leu Thr Val Leu Tyr Gln Tyr
305                 310                 315                 320

Glu Ile Glu Gly Leu Glu Val Leu Thr Lys Asp Glu Lys Trp Ile Arg
                325                 330                 335

Leu Lys Pro Ser His Asn Ser Phe Val Val Met Ala Gly Asp Ser Leu
            340                 345                 350

Tyr Ala Leu Met Asn Gly Arg Leu Ser Arg Pro Phe His Arg Val Arg
        355                 360                 365

Val Thr Glu Arg Lys Lys Thr Arg Tyr Ser Ile Ala Leu Phe Ser Thr
    370                 375                 380
```

-continued

```
Pro Asn Gly Asp Tyr Ile Ile Glu Pro Pro Lys Glu Leu Val Asp Glu
385                 390                 395                 400

Lys His Pro Arg Leu Phe Lys Pro Phe Thr Tyr Val Asp Leu Met Ser
            405                 410                 415

Phe Tyr His Thr Glu Ala Gly Arg Arg Pro Arg Ser Thr Leu His Ala
            420                 425                 430

Tyr Cys Ala Val Ser Gly Ala
            435

<210> SEQ ID NO 41
<211> LENGTH: 322
<212> TYPE: PRT
<213> ORGANISM: Arabidopsis thaliana
<220> FEATURE:
<223> OTHER INFORMATION: 2-oxoglutarate-dependent dioxygenase (ODD) 1
      from ecotype Columbia (Atcol1)

<400> SEQUENCE: 41

Met Asp Ser Asp Phe Val Pro Pro Ser Val Ser Phe Gln Leu Pro Val
  1               5                  10                  15

Ile Asp Phe Ser Asp Gln Asn Leu Lys Pro Gly Ser Ser Lys Trp Asp
             20                  25                  30

Glu Val Thr Ala Asp Val Leu Lys Ala Leu Glu Asp Tyr Gly Cys Phe
         35                  40                  45

Glu Ala Ser Phe Asp Lys Leu Ser Val Glu Leu Asn Arg Ser Val Phe
     50                  55                  60

Glu Ala Met Glu Asp Leu Phe Glu Leu Pro Ile Pro Thr Lys Gln Arg
 65                  70                  75                  80

Asn Val Ser Ser Lys Pro Phe His Gly Tyr Leu Cys His Asn Leu Tyr
                 85                  90                  95

Glu Ser Leu Gly Ile Asn Asp Ala Asn Val Leu Glu Lys Val Asn Asp
            100                 105                 110

Phe Thr Gln Gln Leu Trp Pro Asp His Gly Asn Lys Ser Ile Ser Glu
        115                 120                 125

Thr Ile His Leu Phe Ser Glu Gln Leu Val Glu Leu Asp Leu Met Val
    130                 135                 140

Arg Arg Met Ile Met Glu Ser Phe Gly Ile Glu Asn Tyr Ile Asp Glu
145                 150                 155                 160

His Leu Asn Ser Thr Tyr Tyr Leu Thr Arg Leu Met Lys Tyr Thr Ser
                165                 170                 175

Pro Pro Asp Asp Asp Asp Asp Glu Glu Thr Lys Leu Gly Leu
            180                 185                 190

Arg Ser His Thr Asp Lys Asn Ile Ile Thr Ile Leu His Gln Tyr Gln
        195                 200                 205

Val Asp Gly Leu Glu Val Lys Thr Lys Asp Asp Lys Trp Ile Lys Val
    210                 215                 220

Lys Pro Ser Gln Asp Ser Val Leu Val Met Val Gly Asp Ser Leu Cys
225                 230                 235                 240

Ala Leu Leu Asn Gly Arg Leu His Ser Pro Tyr His Arg Val Ile Met
                245                 250                 255

Thr Gly Lys Lys Thr Arg Tyr Ser Thr Gly Leu Phe Ser Ile Pro Lys
            260                 265                 270

Thr Gly Val Ile Ile Asp Ser Pro Glu Glu Leu Val Asp Lys Glu His
        275                 280                 285

Pro Arg Ile Phe Lys Pro Phe Glu Tyr Thr Asp Phe Leu His Phe Phe
```

```
                    290                 295                 300
Gln Thr Glu Ala Gly Arg Ile Ala Gln Ser Ala Leu His Ala Phe Ala
305                 310                 315                 320

Ala Phe
```